(12) United States Patent
Fosdick et al.

(10) Patent No.: US 9,999,240 B2
(45) Date of Patent: *Jun. 19, 2018

(54) CARBOHYDRATE COMPOSITIONS

(71) Applicant: Cargill, Incorporated, Wayzata, MN (US)

(72) Inventors: Lawrence E. Fosdick, Troy, OH (US); Scott Helstad, Dayton, OH (US); Yauching W. Jasinski, Dayton, OH (US); Guo-hua Zheng, Centerville, OH (US)

(73) Assignee: Cargill, Incorporated, Wayzata, MN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/656,801

(22) Filed: Jul. 21, 2017

(65) Prior Publication Data

US 2017/0318850 A1 Nov. 9, 2017

Related U.S. Application Data

(60) Continuation-in-part of application No. 14/611,835, filed on Feb. 2, 2015, now Pat. No. 9,730,464, which is a continuation-in-part of application No. 13/835,330, filed on Mar. 15, 2013, which is a division of application No. 13/724,902, filed on Dec. 21, 2012, which is a division of application No. 12/991,868, filed as application No. PCT/US2009/043488 on May 11, 2009, now Pat. No. 8,361,235.

(60) Provisional application No. 61/127,023, filed on May 9, 2008.

(51) Int. Cl.
| | |
|---|---|
| A23L 2/60 | (2006.01) |
| A23L 33/125 | (2016.01) |
| C13B 10/00 | (2011.01) |
| A23L 13/50 | (2016.01) |
| A23L 13/40 | (2016.01) |
| A23L 27/60 | (2016.01) |
| A23L 29/30 | (2016.01) |
| A23L 21/10 | (2016.01) |
| A23L 7/126 | (2016.01) |
| C13K 1/06 | (2006.01) |
| C12P 19/14 | (2006.01) |
| C12P 19/12 | (2006.01) |
| C12P 19/04 | (2006.01) |
| C12P 19/02 | (2006.01) |
| A23G 9/34 | (2006.01) |
| A23G 4/10 | (2006.01) |
| A23G 3/42 | (2006.01) |
| A23G 1/40 | (2006.01) |
| A23C 9/156 | (2006.01) |
| A23C 9/13 | (2006.01) |
| A21D 13/062 | (2017.01) |
| A21D 2/18 | (2006.01) |
| A23L 23/00 | (2016.01) |

(52) U.S. Cl.
CPC ............ *A23L 33/125* (2016.08); *A21D 2/181* (2013.01); *A21D 13/062* (2013.01); *A23C 9/1307* (2013.01); *A23C 9/156* (2013.01); *A23G 1/40* (2013.01); *A23G 3/42* (2013.01); *A23G 4/10* (2013.01); *A23G 9/34* (2013.01); *A23L 2/60* (2013.01); *A23L 7/126* (2016.08); *A23L 13/428* (2016.08); *A23L 13/50* (2016.08); *A23L 21/10* (2016.08); *A23L 23/00* (2016.08); *A23L 27/60* (2016.08); *A23L 29/30* (2016.08); *A23L 29/35* (2016.08); *C12P 19/02* (2013.01); *C12P 19/04* (2013.01); *C12P 19/12* (2013.01); *C12P 19/14* (2013.01); *C13B 10/00* (2013.01); *C13K 1/06* (2013.01)

(58) Field of Classification Search
CPC .................................................... A23L 33/125
See application file for complete search history.

(56) References Cited

U.S. PATENT DOCUMENTS 9,730,464 B2 * 8/2017 Fosdick ............... A23L 13/50

* cited by examiner

*Primary Examiner* — Melvin C. Mayes
*Assistant Examiner* — Stefanie Cohen

(57) ABSTRACT

The invention provides carbohydrate compositions and products comprising the carbohydrate compositions, such as dry products or a low-viscosity reduced-sugar syrup, methods of making the carbohydrate compositions and products, and uses thereof.

15 Claims, 6 Drawing Sheets

CARBOHYDRATE COMPOSITIONS

CROSS REFERENCE TO RELATED APPLICATIONS

This application is a Continuation in Part of Ser. No. 14/611,835, filed Feb. 2, 2015, entitled CARBOHYDRATE COMPOSITIONS AND PRODUCTS COMPRISING CARBOHYDRATE COMPOSITIONS, now U.S. Pat. No. 9,730,464, which is a Continuation in Part of Ser. No. 13/835,330, now abandoned, filed Mar. 15, 2013, entitled CARBOHYDRATE COMPOSITIONS, which is a Divisional of Ser. No. 13/724,902, now abandoned, filed Dec. 21, 2012, entitled LOW-VISCOSITY REDUCED-SUGAR SYRUP, METHODS OF MAKING, AND APPLICATIONS THEREOF, which is a Divisional of U.S. patent application Ser. No. 12/991,868 now U.S. Pat. No. 8,361,235, filed Nov. 9, 2010, now entitled LOW-VISCOSITY REDUCED-SUGAR SYRUP, METHODS OF MAKING, AND APPLICATIONS THEREOF, which is a section 371 national-stage phase of International Application No. PCT/US2009/043488, filed May 11, 2009, entitled LOW-VISCOSITY REDUCED-SUGAR SYRUP, METHODS OF MAKING, AND APPLICATIONS THEREOF, which claims priority to U.S. Provisional Patent Application No. 61/127,023, filed May 9, 2008, entitled LOW-VISCOSITY REDUCED-SUGAR SYRUP AND METHODS OF MAKING, which are hereby incorporated by reference in their entirety.

FIELD

This invention relates to carbohydrate compositions and products comprising the carbohydrate compositions, such as dry products and low-viscosity, reduced-sugar syrup, methods of making such syrup, and uses thereof.

BACKGROUND

Syrups are produced from starch, which is liquefied in the presence of acid or enzymes or both to convert the starch to smaller carbohydrate chains. The particular carbohydrate composition of the syrup is determined by the starting material as well as the acid and/or enzyme used, the temperature and pH at which the starch is liquefied, and the length of time the starch is exposed to the acid and/or enzyme. For example, the conversion of starch can be halted at an early stage resulting predominantly in polysaccharides, which generally produce low-to-medium sweetness syrups with medium-to-low humectancy, or the conversion can be allowed to proceed until the carbohydrates are nearly all dextrose, which generally produce sweet syrups with high hygroscopocity and humectancy.

Syrups are widely used in the manufacture of foods and beverages. In many cases, it is the individual saccharides or groups of saccharides (in other words, the carbohydrate composition) that determine syrup characteristics. Managing moisture is one of the most important functional properties that carbohydrate syrups contribute in various foods. In general, hygroscopicity (the property of adsorping moisture or picking up moisture) and humectancy (the property of retaining moisture or, conversely, not losing moisture) increase with the increase of mono- and di-saccharides or the increase of DE values of syrup products. High conversion starch syrups with more than 25% total mono- and di-saccharides and/or typically a dextrose equivalence (DE) of over 40 to 50 are used in various food products where humectancy is required, such as bakery products and soft chewy bars. Whereas low conversion starch syrups with less than 25% total mono- and di-saccharides and/or typically less than DE of 40 to 50 are used in applications where hygroscopicity needs to be avoided, such as hard candies and cereal coatings. These physiochemical properties are of particular importance to food manufacturing practices. Properties, such as appearance, texture, and mouthfeel of finished foods are also affected by the syrup used because of their physicochemical properties such as sweetness, hygroscopicity, and humectancy attributes.

SUMMARY

The present invention is directed to carbohydrate compositions and products comprising the carbohydrate compositions, such as dry products or a low-viscosity reduced-sugar syrup. In various embodiments, the carbohydrate compositions and products comprising the carbohydrate compositions are surprisingly sweet and have an unexpected high humectancy and an unexpected high hygroscopicity, irrespective of their low (i.e., no more than 25%) mono- and di-saccharide concentrations on a dry weight basis.

In one embodiment, the syrup has reduced sugar and low viscosity, with a DE of 20 to 52 or 26 to 52. The reduced sugar has less than 25% total mono- and di-saccharides, or 0.5% to 25% total mono- and di-saccharides (DP1+2), and the viscosity is significantly lower compared to a starch-derived product that has a similar dry weight percentage of total mono- and di-saccharides.

In a second embodiment, the low-viscosity reduced-sugar syrup with total mono- and di-saccharides of less than 25% has a viscosity not greater than 100,000 cPs at a temperature of 100° F. and 78% DS. In another aspect, the total mono- and di-saccharides is from 10% to 25% on a dry weight basis and the viscosity is not greater than 30,000 cPs at a temperature of 100° F. and 78% DS. In yet another aspect, the total mono- and di-saccharides is from 20% to 25% on a dry weight basis and the viscosity is not greater than 15,000 cPs at a temperature of 100° F. and 78% DS. In still another aspect, the total mono- and di-saccharides is from 0.5% to 10% on a dry weight basis and the viscosity is not greater than 250,000 cPs at a temperature of 100° F. and 78% DS.

In a third embodiment, the low-viscosity reduced-sugar syrup has significantly lower levels of total mono- and di-saccharides of less than 25% of the total carbohydrates, significantly higher levels of oligosaccharides (DP3-14) of greater than 60% of the total carbohydrates, and significantly lower levels of the polysaccharides (DP15+) of less than 15% of the total carbohydrates compared to a conventional starch-derived product that has a similar percentage of total mono- and di-saccharides on a dry weight basis.

In a fourth embodiment, the low-viscosity reduced-sugar syrup has significantly lower levels of total mono- and di-saccharides of less than 25% of the total carbohydrates, significantly higher levels of oligosaccharides (DP3-10) of greater than 60% of the total carbohydrates, and significantly lower levels of polysaccharides of less than 20% of the total carbohydrates compared to a conventional starch-derived product that has a similar percentage of total mono- and di-saccharides on a dry weight basis.

In a fifth embodiment, the low-viscosity reduced-sugar syrup has a DE of from 20 to 52, or a DE of from 26 to 52, and a First Oligosaccharide Index of greater than 2.0. The low-viscosity reduced sugar syrup in a sixth embodiment has a DE of from 20 to 52, or a DE of from 26 to 52, and a Second Oligosaccharide Index of greater than 3.0.

In a seventh embodiment, the low-viscosity reduced-sugar syrup has a less than 25% total mono- and di-saccharides, or 0.5% to 25% total mono- and di-saccharides, and a First Oligosaccharide Index of greater than 2.0. The low-viscosity reduced sugar syrup also in another embodiment has less than 25% total mono- and di-saccharides, or 0.5% to 25% total mono- and di-saccharides, and a Second Oligosaccharide Index of greater than 3.0.

In an eighth embodiment, the carbohydrate composition or dry product or low-viscosity reduced-sugar syrup comprising the carbohydrate composition has a DP5 concentration of up to 3% oligosaccharides, on a dry weight basis, and the total concentrations of DP3+4 ranging from about 50% to about 75% oligosaccharides, or from about 55% to about 65% oligosaccharides, on a dry weight basis.

In a ninth embodiment, the carbohydrate composition or dry product or low-viscosity reduced-sugar syrup comprising the carbohydrate composition has a calculated sweetness of at least 23, such as greater than 25, such as about 29, or ranging from about 23 to about 29 or from about 25 to about 28.

In a tenth embodiment, the carbohydrate composition or dry product or low-viscosity reduced-sugar syrup comprising the carbohydrate composition has a sweetness of approximately 40 to 55, such as about 45, relative to sucrose, or approximately equivalent to the sweetness of a 43DE corn syrup.

In an eleventh embodiment, the carbohydrate composition or dry product or low-viscosity reduced-sugar syrup comprising the carbohydrate composition has a ratio of DP3/DP5 of greater than about 4, such as greater than 11 or ranging from about 4 to about 31.

In a twelfth embodiment, the carbohydrate composition or dry product or low-viscosity reduced-sugar syrup comprising the carbohydrate composition has a ratio of DP2/DP5 of greater than about 4, such as greater than 4.2, greater than 4.5, for example greater than or equal to 9, or ranging from about 4 to about 25.

In a thirteenth embodiment, the carbohydrate composition or dry product or low-viscosity reduced-sugar syrup comprising the carbohydrate composition has a ratio of (DP3+4)/DP5 of at least 16, such as greater than or equal to 20 or ranging from 20 to about 95.

In a fourteenth embodiment, the carbohydrate composition or dry product or low-viscosity reduced-sugar syrup comprising the carbohydrate composition has a total mono- and di-saccharide concentration of less than 25% on a dry weight basis, a DP3 concentration of up to 55%, on a dry weight basis, a DP5 concentration of up to 4.5% oligosaccharides on a dry weight basis; a ratio of DP2/DP5 of at least 4, such as at least 4.2 or at least 4.5; optionally a ratio of DP3/DP5 of greater than 4, such as greater than 4.2, or greater than 4.5; optionally a DP3+DP4 ranging from 50-75%, on a dry weight basis; optionally a calculated theoretical sweetness ranging from 23-28; optionally a sweetness approximately equivalent to that of a 43DE corn syrup or from about 40-55 relative to sucrose; optionally less than 10% DP11+ on a dry weight basis; optionally a viscosity of less than 10,000 cPs or less than 8000 cPs, when measured at 100° F. and 78% DS; and optionally a ratio of (DP3+4)/DP5 of at least 20.

In a fifteenth embodiment, the carbohydrate composition or dry product or low-viscosity reduced-sugar syrup comprising the carbohydrate composition has a total mono- and di-saccharide concentration of less than 25% on a dry weight basis, a DP3 concentration of up to 55%, on a dry weight basis, a DP5 concentration of up to 4.5% oligosaccharides on a dry weight basis; a ratio of DP2/DP5 of at least 4, such as at least 4.2 or at least 4.5; and a sweetness approximately equivalent to that of a 43DE corn syrup or from about 40-55 relative to sucrose; optionally a ratio of DP3/DP5 of greater than 4, such as greater than 4.2, or greater than 4.5; optionally a DP3+DP4 ranging from 50-80%, on a dry weight basis; optionally a viscosity of less than 10,000 cPs or less than 8000 cPs, when measured at 100° F. and 78% DS; and optionally a ratio of (DP3+4)/DP5 of at least 20.

In a sixteenth embodiment, the carbohydrate composition or dry product or low-viscosity reduced-sugar syrup comprising the carbohydrate composition has a DP5 concentration of up to 3% oligosaccharides, a ratio of (DP3+4)/DP5 of at least 20, a ratio of DP3/DP5 greater than about 4, such as greater than 4.2, or greater than 4.5, a ratio of DP2/DP5 of greater than about 4, such as at least 4.2 or at least 4.5, a calculated sweetness ranging from about 25 to about 29, and a sweetness of approximately 40 to 55 relative to sucrose, or approximately equivalent to the sweetness of a 43DE corn syrup.

In a seventeenth embodiment, a low-viscosity reduced sugar syrup comprising a carbohydrate composition or dry product has a total mono- and di-saccharide concentration of 20-24% on a dry weight basis, a DP3-14 concentration of greater than 71%, on a dry weight basis, a DP11+ concentration of less than 7% oligosaccharides and polysaccharides on a dry weight basis; a DP5 concentration of up to 4.5% oligosaccharides on a dry weight basis; a ratio of DP2/DP5 of at least 4, such as at least 4.2 or at least 4.5; and a sweetness approximately equivalent to that of a 43DE corn syrup or from about 40-55 relative to sucrose; optionally a ratio of DP3/DP5 of greater than 4, such as greater than 4.2, or greater than 4.5; optionally a DP3+DP4 ranging from 50-80%, on a dry weight basis; optionally a viscosity of less than 10,000 cPs or less than 8000 cPs, when measured at 100° F. and 78% DS; and optionally a ratio of (DP3+4)/DP5 of at least 20.

In an eighteenth embodiment, the carbohydrate composition or dry product or low-viscosity reduced-sugar syrup comprising the carbohydrate composition has no more than 25% total mono- and di-saccharides on a dry weight basis, from about 50% to about 75% total oligosaccharides with a degree of polymerization from 3 to 4 on a dry weight basis, less than 10% of polymeric carbohydrates with a degree of polymerization of at least 11, and a ratio of DP2/DP5 of at least 4.2, wherein the carbohydrate composition has a higher moisture retention during desorption at relative humidity of less than 90% at 25° C. and ambient pressure, compared to a 36 DE or a 43 DE conventional syrup.

In a nineteenth embodiment, the carbohydrate composition or dry product or low-viscosity reduced-sugar syrup comprising the carbohydrate composition has no more than 25% total mono- and di-saccharides on a dry weight basis, from about 50% to about 75% total oligosaccharides with a degree of polymerization from 3 to 4 on a dry weight basis, less than 10% of polymeric carbohydrates with a degree of polymerization of at least 11, and a ratio of DP2/DP5 of at least 4.2, wherein the carbohydrate composition has a similar moisture retention during adsorption at relative humidity of more than 5 to 90% at 25° C. and at ambient pressure, as a 36 DE conventional syrup.

In a twentieth embodiment, the carbohydrate composition or dry product or low-viscosity reduced-sugar syrup comprising the carbohydrate composition has no more than 25% total mono- and di-saccharides on a dry weight basis, from about 50% to about 75% total oligosaccharides with a degree of polymerization from 3 to 4 on a dry weight basis, less than 10% of polymeric carbohydrates with a degree of polymerization of at least 11, and a ratio of DP2/DP5 of at least 4.2, wherein the carbohydrate composition increases softness, or conversely decreases hardness, by at least 10% of foods containing about 10 to about 70% moisture (w/w) and less than about 50% total mono- and di-saccharides (w/w) when more than about 5% (w/w) of the carbohydrate composition is incorporated into such foods.

Methods of producing the carbohydrate compositions and/or syrups of any of the above- or below described embodiments are also contemplated. In one embodiment the methods comprise liquifying a starch composition at 10-50% dry solid concentration at a temperature ranging from about 90-150° C. with at least one heat-stable alpha-amylase or inorganic acid; adding at least one additional alpha amylase, optionally with a debranching enzyme; and holding the liquifect at a temperature of about 70° C. to about 95° C. for a time sufficient to hydrolyze the starch composition to form a carbohydrate composition or syrup according to any of the above- or below-described embodiments.

Food, beverage, animal feed, cosmetic, and/or pharmaceutical products incorporating any of the above- or below-described embodiments are also contemplated.

The details of one or more embodiments of the invention are set forth in the accompanying drawings and the description below. Other features, objects, and advantages of the invention will be apparent from the drawings and detailed description, and from the claims.

DETAILED DESCRIPTION

Terms and Definitions

Figure 1:
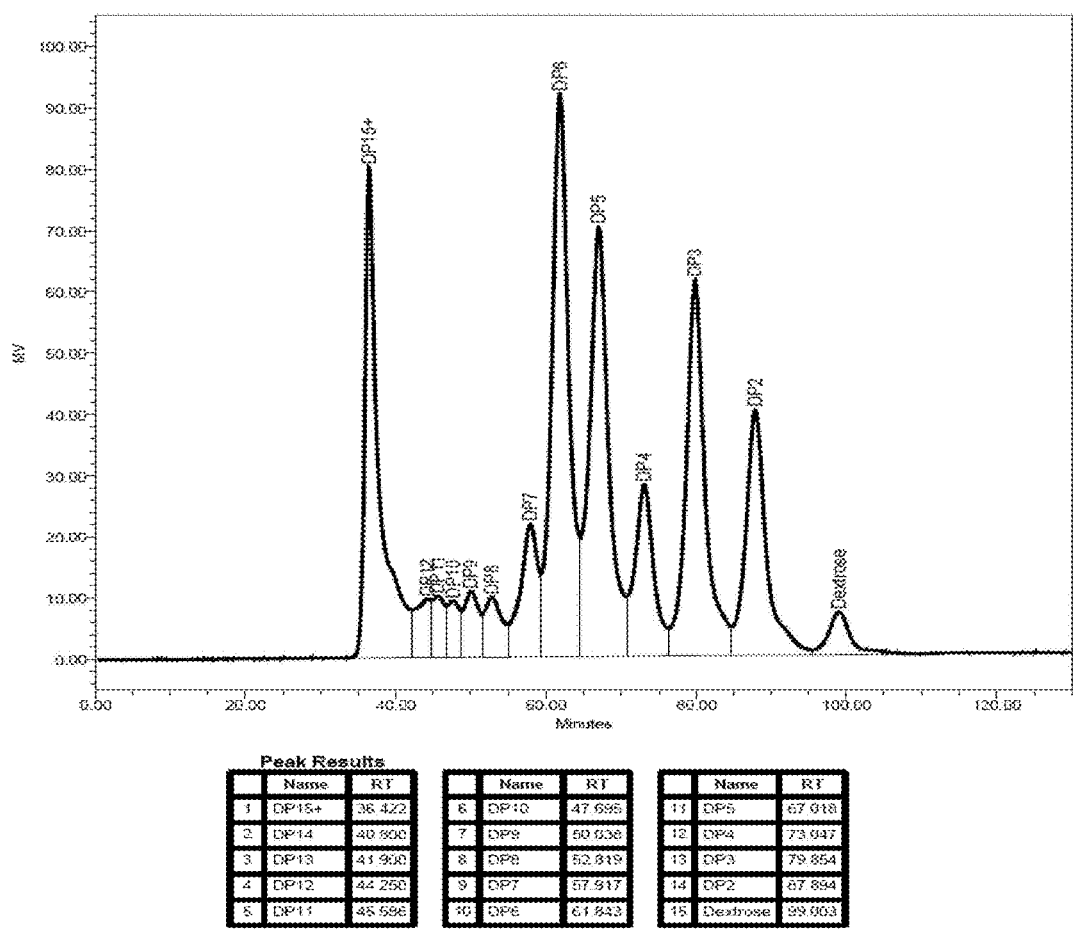
FIG. 1 is a chromatograph showing the DP composition of the low-viscosity reduced-sugar syrup in Example 1.

Unless otherwise defined, all technical and scientific terms used herein have the same meaning as commonly understood by one of ordinary skill in the art to which this invention belongs.

The term, "bodying", as used herein, refers to additives used to impart desirable body, viscosity and consistency to foods.

The term, "dextrose equivalent" or "DE", as used herein, interchangeably refer to the degree of starch hydrolysis, specifically, the reducing value of a starch hydrolysate material compared to the reducing value of an equal weight of dextrose, expressed as percent, dry basis, as measured by the Lane and Eynon method described in Standard Analytical Method E-26, Corn Refiners Association, $6^{th}$ Edition, 1977, E-26, pp. 1-3.

The term, "DP-N", as used herein, refers to the degree of polymerization, where N is the number of monomeric units (i.e., glucose or dextrose units) in the saccharide, thus DP-N reflects the composition of the carbohydrate. For example, DP1 is a monosaccharide and refers only to dextrose; DP2 is a disaccharide and refers only to maltose; DP1+2 is the total of mono- and di-saccharides; DP3-10 is the total of DP 3 to DP10; DP11+ is the total of saccharides DP11 and greater. Further, as used herein, DP3 refers only to maltotriose; DP4 refers only to maltotetraose; and DP5 refers only to maltopentaose.

The ratio of DP3 to DP10 divided by DP11+ is referred to as First Oligosaccharide Index, and the ratio of DP3 to DP14 divided by DP15+ is referred to as Second Oligosaccharide Index. DP-N is expressed as a weight percent of an individual saccharide on a total carbohydrate dry weight basis.

It is noted that, typically, sweetness of a syrup decreases as DP increases and vice versa. Also, typically, viscosity of a syrup increases as DP increases and vice versa. The DP-N composition of a starch-derived product was determined using high performance liquid chromatography (HPLC). A sample of low-viscosity reduced-sugar syrup was diluted with deionized water to 5% to 10% DS, de-ashed with ion exchange resins (Dowex 66 and Dowex 88, Dow Chemical Co., Midland, Mich.), and filtered through a 0.45 micron filter before injection into the HPLC for DP carbohydrate analysis. DP separation was accomplished using two BioRad Aminex HPX-42A, 300 mm×7.8 mm columns (BioRad, Hercules, Calif.) in series using water as the eluent at a flow rate of 0.20 ml/min at 65° C. Separated DP was quantitated with a refractive index detector The term, "DS", as used herein, refers to the percent dry solids as determined using the computer program, Refractive Index Dry Substance (RI-DS), Standard Analytical Method E-54, Corn Refiners Association, $6^{th}$ Edition, 1977, E-54, pp. 1-11.

The term, "moisture retention", as used herein, refers to the capacity of the syrup comprising the carbohydrate compositions described herein or food products containing carbohydrate compositions described herein to hold moisture as determined by moisture sorption isotherm test. This property is also referred to as "humectancy". Moisture sorption isotherm (i.e., moisture adsorption and moisture desorption) describes the relationship between equilibrium moisture content and water activity at a constant temperature. At equilibrium, the relationship between water content and equilibrium humidity of a material can be displayed graphically by a curve. The moisture sorption isotherm profiles of the syrup comprising the carbohydrate compositions described in Examples 10 and 11 and the conventional corn syrups of 28, 36, and 43 DE were determined using an IGAsorp Dynamic Vapor Sorption (DVS) analyzer (Hiden Isochema, Warrington, United Kingdom). A syrup sample of about 10 mg was placed in the sample holder that was held at 25° C. and ambient pressure. For the determination of adsorption (i.e., hygroscopicity or moisture gain/moisture uptake), the sample was first allowed to equilibrate at an average relative humidity of 6.4%, then relative humidity was increased step-wise to 20%, 30%, 40%, 50%, 60%, 70%, 80% and finally 90% with relative humidity controlled air. Moisture uptake was monitored with a microbalance equipped with an IGAsorp. Then, relative humidity was decreased step-wise from 90% to 85%, 75%, 65%, 55%, 45%, 35%, 25%, 15% and finally 5% with relative humidity controlled air to determine desorption (i.e., humectancy or moisture retention) by monitoring moisture loss.

The term, "oligosaccharide" as used herein, refers to a starch-derived product with a DP of from at least 3 to at the most 14. For example, DP3-7 is an oligosaccharide, DP3-10 is an oligosaccharide; DP3-14 is an oligosaccharide; DP4-6 is an oligosaccharide.

The term, "polysaccharide", as used herein, refers to a starch-derived product with a DP of at least 15. For example, DP15+ is a polysaccharide.

The term, "short texture", as used herein, refers to the cohesiveness of a starch-derived product when it is pulled apart and how elongated or stringy the binding material is. A starch-derived product having a short texture will not have a lot of elasticity when pulled apart, but will have small "strings" and/or short peaks when pulled apart and may return to its shape.

The term, "similar", as used herein with regard to DP-N, refers to a conventional starch-derived product of total mono- and di-saccharides (DP1+2)±3. As used herein with regard to DE, "similar" refers to a conventional starch-derived product of DE±3.

The term, "smooth mouthfeel", as used herein, refers to a light and creamy consistency on the tongue and in the mouth as compared to more viscous syrup.

The term, "starch-derived product", as used herein, refers to a product obtained from the hydrolysis of starch.

The term "sugar", as used herein, refers to a nutritive carbohydrate sweetener consisting of mono- and/or di-saccharides.

The term, "syrup", as used herein, refers to aqueous solutions of sugars or starch hydrolysates.

The term, "viscosity", as used herein, refers to the resistance of a fluid to flow. The viscosity of a syrup is typically affected by temperature and solid concentration. Viscosity is expressed in terms of centipoise (cP) at a given temperature and a given % DS. Brookfield viscometer (model LVDV-E 115, Brookfield Engineering Inc., Middlesboro, Mass.) with a 12-mL small sample adapter was employed for the determination of viscosity. Temperature of the small sample adapter was controlled using a circulation water bath. Spindle #S-25 was used while rotation speed was varied so that the percent torque fell between 25% to 75% during the viscosity measurements.

The term, "sweetness," as used herein, refers to the sweet sensory impression of the syrup to humans. Sweetness may be measured relative to sucrose, which is considered generally and for purposes of the disclosure to have a sweetness of 100, or may be measured relative to a product that has a known sweetness, such as, for example, a 36DE corn syrup (sweetness of 30-40 relative to sucrose) or a 43DE corn syrup (sweetness of 40-50 relative to sucrose). Sweetness of the syrup was determined by trained and experienced panelists using sucrose ('table sugar') as the reference. The term "calculated sweetness" or "theoretical sweetness," as well as variations thereof, as used herein is a measure of the cumulative amounts by weight of each saccharide (e.g., glucose or dextrose, maltose, maltotriose, etc.) present in the composition, multiplied by the sweetness of each saccharide as reported by Nakakuni (Teruo Nakakuni, 1993. Maltooligosaccharides. In: Oligosaccharides Production, Properties, and applications. Ed. Teruo Nakakuni. Gordon and Breach Science Publishing). For saccharides of DP8 and greater, a sweetness value of 0.05 was assumed when calculating theoretical sweetness.

According to various embodiments, syrups and/or dry products disclosed herein may comprise the carbohydrate compositions described. Dry products comprising the carbohydrate compositions may be prepared by known methods, for example by freeze-drying, spray drying, fluidized-bed drying, rotary drying, tunnel drying, tray or cabinet drying a syrup or other liquid comprising the carbohydrate composition to form a dry product, such as a powdered dry product. Dry products typically have moisture levels of less than about 10%, such as less than about 5%. Syrups, which are typically viscous liquids, comprising the carbohydrate compositions may be prepared as described below. According to one exemplary and non-limiting embodiment, dry products comprising the carbohydrate compositions according to the disclosure may be prepared by drying the syrups described herein to form a dry powdered product, although other methods of preparing a dry product are contemplated. It should be understood that the disclosure describes the carbohydrate compositions with respect to syrups for ease of reference only, and that dry products comprising the carbohydrate compositions as described herein are intended to be within the scope of the disclosure.

The Syrup

The chemical, physical, and functional properties of sweeteners vary according to their carbohydrate compositions. In order to understand the functional and nutritional properties of syrups, the actual carbohydrate composition (or "DP-N") is most useful, though historically DE is also used. Syrups used to be classified into four types on the basis of DE: type I having a DE of about 20 to 38; type II having a DE of 38 to 58; type III having a DE of 58 to 73 and type IV having a DE of 73 and above. With respect to the carbohydrate composition of syrups, the sweetener industry produces starch-derived products typically containing 15% to 99% total mono- and di-saccharides (DP1+2), with the most widely used syrups containing more than 25% total mono- and di-saccharides. Generally, syrups having less than 25% total mono- plus di-saccharides are not very sweet and are extremely viscous and thick, making it a processing challenge to use such syrups due to, for example, high resistance to pumping, high resistance to flow, high adhesiveness to processing equipment, and being prone to microbial contamination. On the other hand, syrups with low viscosities, typically containing more than 25% total mono- and di-saccharides, do not have the processing challenges compared to syrups with less than 25% total mono- and di-saccharides, but they impart added sugar levels to foodstuffs where added sugar levels may not be desired. Thus, there is still a need to provide a syrup with low viscosity for ease of use and at the same time with reduced total mono- and di-saccharide levels for use in food, beverage, and pharmaceutical products where added sugar levels are not desired, but rather a sweet taste is desired.

Food and beverage manufacturers continually seek new product and flavor opportunities to extend their existing product lines, develop new products, or reduce certain nutritional aspects of conventional products, such as reduced sugar. One consequence of reducing sugars is reduced sweetness which often results in unacceptable sensory impression by consumers. Reduced-sugar, sweet-tasting syrups or syrups having binding, bodying, bulking, coating, and water retention characteristics would allow food and beverage manufacturers to develop products not possible with today's conventional syrups or maltodextrins. In one embodiment, the inventors of the present invention have surprisingly found low-viscosity reduced-sugar syrup that is sweet tasting with binding, bodying, bulking, coating, and water retention characteristics. This sweet tasting, low-viscosity reduced-sugar syrup addresses an unmet need across a range of product categories, including for example bars, jams and jellies, fruit confectionaries. In addition, using a sweet tasting, low viscosity reduced-sugar syrup of the present invention also allows food and beverage manufacturers to replicate original flavors, but with less sugar and without the need to mask unwanted flavors.

The present invention relates to a low-viscosity reduced-sugar syrup. In one embodiment, the syrup has reduced sugar and low viscosity, with a DE of about 20 to about 52 or about 26 to about 52. The reduced sugar has less than about 25% total mono- and di-saccharides or about 0.5% to about 25% total mono- and di-saccharides, and the viscosity is significantly lower compared to a starch-derived product that has a similar dry weight percentage of total mono- and di-saccharides. The viscosity in one aspect of the present invention is lower, from about 10% to about 99%, compared to the viscosity of a starch-derived product that has a similar dry weight percentage of total mono- and di-saccharides. The viscosity in a second aspect of the present invention is lower, from about 30% to about 95%, compared to the viscosity of a starch-derived product that has a similar dry weight percentage of total mono- and di-saccharides. In another aspect of the present invention, the viscosity of the low-viscosity reduced-sugar syrup is lower, from about 60% to about 95%, compared to the viscosity of a starch-derived product that has a similar dry weight percentage of total mono- and di-saccharides. In yet another aspect of the present invention, the viscosity of the low-viscosity reduced-sugar syrup is lower, from about 40% to about 75%, compared to the viscosity of a starch-derived product that has a similar dry weight percentage of total mono- and di-saccharides.

The viscosity of the low-viscosity, reduced-sugar syrup may be lower when the viscosity is measured at a given DS and a given temperature as compared to a starch-derived product that has a similar dry weight percentage of total mono- and di-saccharides. In one embodiment, the low-viscosity reduced-sugar syrup with total mono- and di-saccharides of about 25% has a viscosity not greater than about 100,000 cPs at a temperature of about 100° F. and about 78% DS. In a second embodiment, the low-viscosity reduced-sugar syrup with total mono- and di-saccharides ranging from about 20% to about 25%, and total DP3+4 ranging from about 55% to about 65%, has a viscosity not greater than about 15,000 cPs, such as not greater than about 12,000 cPs, not greater than about 10,000 cPs, not greater than 9,000 cPs, or not greater than about 8,000 cPs, when measured at a temperature of about 100° F. and about 78% DS. In another embodiment, the low-viscosity reduced-sugar syrup with total mono- and di-saccharides of from about 10% to about 20% has a viscosity no greater than about 30,000 cPs at a temperature of about 100° F. and about 78% DS. In yet another embodiment, the low-viscosity reduced-sugar syrup with total mono- and di-saccharides of from about 0.5% to about 10% has a viscosity no greater than about 250,000 cPs at a temperature of about 100° F. and about 78% DS.

The low-viscosity reduced-sugar syrup surprisingly has a very different carbohydrate composition from conventional starch-derived products that have a similar percentage of total mono- and di-saccharides on a dry weight basis. In one embodiment, the low-viscosity reduced-sugar syrup has significantly lower levels of total mono- and di-saccharides (DP1+2) of less than about 25% of the total carbohydrates, significantly higher levels of oligosaccharides (DP3–14) of greater than about 60%, such as greater than about 70%, of the total carbohydrates, and significantly lower levels of the polysaccharides (DP15+) of less than about 15%, such as less than about 10% or less than about 6%, of the total carbohydrates compared to a conventional starch-derived product that has a similar percentage of total mono- and di-saccharides on a dry weight basis. In another embodiment, the low-viscosity reduced-sugar syrup has significantly lower levels of total mono- and di-saccharides (DP1+2) of less than about 25% of the total carbohydrates, significantly higher levels of oligosaccharides (DP3–10) of greater than about 60% of the total carbohydrates, and significantly lower levels of the polysaccharides (DP15+) of less than about 20% of the total carbohydrates compared to a conventional starch-derived product that has a similar percentage of total mono- and di-saccharides on a dry weight basis. In at least one embodiment, the low-viscosity reduced-sugar syrup has total polysaccharides (DP11+) of less than about 10%, such as less than about 7%.

In still another embodiment of the present invention, the low-viscosity reduced-sugar syrup has a very different carbohydrate composition compared to conventional starch-derived products having similar DE. In one aspect of the present invention, the low-viscosity reduced-sugar syrup has a DE of from about 20 to about 52 or from about 26 to about 52, and less than about 20%, such as less than 10%, polysaccharides with DP11+ and thus a much higher First Oligosaccharide Index of greater than about 2.0 compared to a conventional starch-derived product having a similar DE. In another aspect of the present invention, the low viscosity reduced-sugar syrup has a DE of from about 20 to about 52 or from about 26 to about 52, and less than about 15%, such as less than 10%, polysaccharides with DP15+ and thus a much higher Second Oligosaccharide Index of greater than about 3.0 compared to a conventional starch-derived product having a similar DE.

In various further embodiments, a low-viscosity reduced-sugar syrup having a carbohydrate composition with a DP1+2 ranging from about 10% to about 25%, such as about 20% to about 23%; a DP3+4 ranging from about 50% to about 75%, such as about 55% to about 65%, or about 56% to about 61%, or about 58% to about 60%; a DP3–14 of greater than about 60%, such as greater than about 70% or greater than 71%; a ratio of DP3/DP5 of greater than 4, such as greater than 11, or ranging from about 4 to about 31, such as about 11 to about 31, or about 11 to about 18; a ratio of (DP3+4)/DP5 of at least 16, or at least 20, or ranging from about 20 to about 95, such as about 30 to about 60; and a ratio of DP2/DP5 of greater than about 4, such as greater than or equal to 9, or ranging from about 4 to about 25, such as about 9 to about 25, or about 9 to about 15, may be unexpectedly sweet. For example, the sweetness of the low-viscosity reduced-sugar syrup may be approximately equivalent to that of a 43DE corn syrup, for example ranging from about 40 to about 55, such as from about 40 to about 45, about 45 to about 50, about 50 to about 55, about 42 to about 46, or about 42, about 43, about 44, about 45, or about 46, compared to the sweetness of sucrose. In further exemplary embodiments, the sweetness of the low-viscosity reduced-sugar syrup may be approximately equivalent to 50, relative to sucrose. The calculated sweetness of the low-viscosity reduced-sugar syrup, based on the carbohydrate profile, may be at least about 22, such as greater than about 23, or, for example, about 25. In at least one embodiment, the calculated sweetness of the low-viscosity reduced-sugar syrup ranges from about 22 to about 28, such as about 26 to about 28.

For example, in at least one embodiment, the low-viscosity, reduced-sugar syrup comprises from 20% to 25% total mono- and di-saccharides, on a dry weight basis; greater than 70% oligosaccharides with a degree of polymerization of from about 3 to about 14, on a dry weight basis; less than about 10% oligosaccharides and polysaccharides with a degree of polymerization of about at least 11, on a dry weight basis; up to 3% oligosaccharides with a degree of polymerization of 5, on a dry weight basis; and from about 50% to about 75% oligosaccharides with a degree of polymerization from 3 to 4, on a dry weight basis. The syrup may have a (DP3+4)/DP5 ratio of at least 16 or at least 20, and/or a DP3/DP5 and/or a DP2/DP5 ratio of greater than 4. For example, the (DP3+4)/DP5 ratio may range from 20 to 95, or may be greater than 30, and the DP3/DP5 ratio may range from 4 to 31, or may be greater than 11, and DP2/DP5 ratio may range from 4 to 25, or may be greater than or equal to 9. The syrup may have a viscosity of less than about 10,000 cPs, such as less than about 9,000 cPs or less than about 8,000 cPs, such as about 7,400 cPs, when measured at a temperature of about 100° F. and about 78% DS. The syrup may have a calculated sweetness greater than 22, such as greater than 23, such as about 29, or may range from 23 to 28. The syrup may have a sweetness of approximately equivalent to or greater than a 43DE corn syrup, or about 40 to about 55 as compared to 100 of sucrose.

As a further example, in another embodiment, the low-viscosity, reduced-sugar syrup comprises from 21% to 24% total mono- and di-saccharides, on a dry weight basis; greater than 70% oligosaccharides with a degree of polymerization of from about 3 to about 14, on a dry weight basis; less than about 10% oligosaccharides and polysaccharides with a degree of polymerization of about at least 11, on a dry weight basis; up to 3% oligosaccharides with a degree of polymerization of 5, on a dry weight basis; and from about 55% to about 65% oligosaccharides with a degree of polymerization from 3 to 4, on a dry weight basis. The syrup may have a DP(3+4)/DP5 least 20, and/or a DP3/DP5 and/or a DP2/DP5 ratio of greater than 4. For example, the DP(3+4)/DP5 ratio may range from 20 to 95, or may be greater than 30, the DP3/DP5 ratio may range from 4 to 31, or may be greater than 11, and DP2/DP5 ratio may range from 4 to 25, or may be greater than or equal to 9. The syrup may have a viscosity of less than about 10,000 cPs, such as less than about 9,000 cPs or less than about 8,000 cPs, such as about 7,400 cPs, when measured at a temperature of about 100° F. and about 78% DS. The syrup may have a calculated sweetness greater than 22, such as greater than 25, such as about 29, or may range from 23 to 28. The syrup may have a sweetness of approximately equivalent to the sweetness of a 43DE corn syrup, or about 40 to about 55 relative to sucrose.

In yet a further exemplary embodiment, the low-viscosity, reduced-sugar syrup comprises from 21% to 23% total mono- and di-saccharides, on a dry weight basis; greater than 71% oligosaccharides with a degree of polymerization of from about 3 to about 14, on a dry weight basis; less than about 7% oligosaccharides and polysaccharides with a degree of polymerization of about at least 11, on a dry weight basis; up to 3% oligosaccharides with a degree of polymerization of 5, on a dry weight basis; and from about 56% to about 61% oligosaccharides with a degree of polymerization from 3 to 4, on a dry weight basis. The syrup may have a DP(3+4)/DP5 least 20, and/or a DP3/DP5 and/or a DP2/DP5 ratio of greater than 4. For example, the DP(3+4)/DP5 ratio may range from 20 to 95, or may be greater than 30, the DP3/DP5 ratio may range from 4 to 31, or may be greater than 11, and DP2/DP5 ratio may range from 4 to 25, or may be greater than or equal to 9. The syrup may have a viscosity of less than about 10,000 cPs, such as less than about 9,000 cPs or less than about 8,000 cPs, such as about 7,400 cPs, when measured at a temperature of about 100° F. and about 78% DS. The syrup may have a calculated sweetness greater than 22, such as greater than 23, such as about 29, or may range from 23 to 28. The syrup may have a sweetness of approximately equivalent to the sweetness of a 43DE corn syrup, or about 40 to about 55 relative to sucrose.

Methods of Preparing the Syrup

The low-viscosity reduced-sugar syrup of the present invention can be made using methods that are routinely practiced in the art. Syrups are produced from starch, which is liquefied in the presence of acids or enzymes or both to convert the starch to sugars. For example, an aqueous starch slurry containing about 35% to about 50% starch dry solid is acid-converted using about 0.015-0.025N hydrochloric acid at temperature range of about 250° F. to about 320° F. for a given time length. Alternatively, the aqueous starch slurry is adjusted to a desired pH, then enzymatically converted with an alpha-amylase at about 0.05-0.1% inclusion level at a temperature of about 180° F. to about 230° F. for a given time. The particular sugar composition of the syrup is determined by the starting material as well as the acid and/or enzyme used, the temperature and pH at which the starch is liquefied, and the length of time the starch is exposed to the acid and/or enzyme. For example, the conversion of starch to sugars can be altered at an early stage resulting in predominantly polysaccharides, which generally produces low-to-medium sweetness syrups and are very viscous, or the conversion can be allowed to proceed until the carbohydrates are nearly all dextrose, which generally produces very sweet syrups with very low viscosities. After liquefaction of starch into syrup, the syrup can be refined using filters, centrifuges, granular activated carbons or ion-exchange resins, and excess water can be removed.

Generally, a starch stream is partially converted into syrup by acid-hydrolysis, typically under heat and pressure for varying amounts of time depending upon the desired properties, or by enzyme-hydrolysis under controlled temperature and pH conditions for varying amounts of time depending upon the desired properties. The resulting syrup can be filtered or otherwise clarified to remove any objectionable flavor or color, and further refined and evaporated to reduce the amount of water. In the acid-enzyme process, starch is first partially hydrolyzed or liquefied by forming an aqueous suspension containing starch and incorporating therein an acid such as hydrochloric acid. The suspension is then heated to high temperatures to partially hydrolyze the starch. The suspension may be cooled and treated at a suitable concentration and pH range to enzymatically convert the partially hydrolyzed starch. In the enzyme-enzyme conversion process, generally, a starch slurry is formed and a starch liquefying enzyme is added and the starch slurry heated to partially hydrolyze the starch. The partial hydrolysis is usually carried out at a specific temperature range. Any suitable starch liquefying enzyme may be used to partially hydrolyze the starch. The partially hydrolyzed starch slurry may then be treated to convert the starch.

Starch can be obtained from a number of different sources using any number of methods routinely practiced in the art. For example, starch can be obtained from corn or another cereal feedstock such as rice, wheat, barley, oats, or sorghum through well known wet-milling and dry-milling techniques. In wet milling, corn or other feedstock can be steeped for a period of time and then ground to separate the germ, which contains the oil, from the other components. The remaining non-germ material is a slurry that includes starch, protein (e.g., gluten) and fiber, which can be separated into different streams. Starch steams also can be obtained from corn or another starch-rich feedstocks through dry milling techniques, which also are practiced routinely in the art. In addition, starch streams can be obtained from a root or tuber feedstock such as potato or cassava using either wet-milling or dry-milling processes.

To produce the unique low-viscosity reduced-sugar syrup described herein, in one embodiment, a starch is made to a slurry of about 10% to about 70% DS and partially converted (either by acid- or enzyme-hydrolysis) to a starch liquor having a DE from about 1 to about 65, which is contacted with pullulanase enzyme, isoamylase enzyme, amylase enzyme, either alone or in combinations thereof. The inventors of the present invention have surprisingly found that a reduced-sugar syrup is produced to have an unexpected low viscosity when specific enzymes and their combinations are used to treat specifically chosen starch liquor under specific pH, temperature and time conditions. In one aspect, from about 0.001% to about 1.0% of such enzymes, alone or in combination, is used based on the total dry weight of the starch. In another aspect, from about 0.01% to about 0.8% of such enzymes is used.

The unique syrup described herein is produced by hydrolyzing the starch liquor in the presence of about 0.001% to about 1% of amylase, isoamylase, pullulanase enzymes based on the total dry weight of the starch, alone or in combinations, at a pH of from about 3.0 to about 7.0 (e.g. pH about 3.0, pH about 3.5 to about 7.0, pH about 4.0 to about 7.0, pH about 4.5 to about 7.0, pH about 5.0 to about 7.0, pH about 5.5 to about 7.0, pH about 6.0 to about 7.0, pH about 6.5 to about 7.0, pH about 3.0 to about 6.5, pH about 3.0 to about 6.0, pH about 3.0 to about 5.5, pH about 3.0 to about 5.0, pH about 3.0 to about 4.5, pH about 3.0 to about 3.5, or pH about 7.0) and a temperature of about 110° F. to about 160° F. (e.g., about 110° F., about 115° F., about 120° F., about 125° F., about 130° F., about 135° F., about 140° F., about 145° F., about 150° F., about 155° F., or about 160° F.) for about 5 to 45 hours (e.g., about 5 to 15 hours, about 15 to 25 hours, about 25 to 45 hours, about 12 to 45 hours, about 12 to 40 hours, or about 25 to 45 hours). It would be understood by those of skill in the art that the amount of both enzymes and the period of time of exposure to such enzymes (as well as the temperature at which such exposure takes place) can be adjusted accordingly so as to obtain a syrup having the DE and the accompanying DP profile and viscosity described herein. The amylase, isoamylase, and pullulanase enzymes can be obtained from commercial sources such as Sigma Chemical Co. (St. Louis, Mo.), Novozymes A/S (Krogshoejvej 36, 2880 Bagsvaerd, Denmark) Danisco A/S including Genencor (Langebrogade 1, 1001 Copenhagen, Denmark), Enzyme Development Corporation (360 West 31$^{st}$ Street, Suite 1102, New York, N.Y. 10001-2727), Verenium Corporation (Cambridge, Mass.), Amano Enzymes Inc. (1-2-7, Nishiki, Naka-ku, Nagoya 460-8630 Japan), Hayashibara (1-2-3 Shimoishii, Okayama 700-0907, Japan) or purified from natural or recombinant sources using known methods. It is noted that with the new recombinant gene technologies, it is possible for new enzymes to be more effective at temperatures higher than about 160° F. In contrast, at a temperature of about 110° F. to about 150° F., low-temperature enzymes will be more effective.

Properties and Applications of the Syrup

The unique carbohydrate composition of the present invention results in a low-viscosity syrup, which allows more water to be removed from the syrup, resulting in increased dry solid concentration in the finished syrup products and decreased water activity. Therefore, microbial stability is improved in low-viscosity reduced-sugar syrup as compared to conventional syrups that have similar total mono- and disaccharides.

Various embodiments of the reduced-sugar syrup of the present invention, having a unique carbohydrate composition and low-viscosity, offer properties that are of particular importance to food manufacturing practices and the properties of finished foodstuffs. For example, in one embodiment these properties include low adhesiveness to processing equipment, capacity of moisture retention, high rates of flow and more easily pumped particularly at low temperatures, short texture, imparting texture to finished foods, and imparting smooth mouthfeel to finished foods and beverages. In a further exemplary embodiment, the properties may include a sweet taste, wherein the sweetness level is approximately equivalent to that of a 43DE corn syrup, or about 40-55, relative to sucrose. In yet a further exemplary embodiment, the properties may include increased moisture retention, wherein the level of moisture retention is approximately equivalent or higher than 43DE corn syrup (i.e., the carbohydrate compositions of the present invention. Furthermore, the properties may include a hygroscopicity or the capability of moisture adsorption (moisture pickup) similar to a 36DE corn syrup. The low-viscosity reduced-sugar syrup of the present invention can be utilized in food, beverage, and pharmaceutical products to decrease the sugar content of such products with minimal impact on the physical properties of such products; and at the same time with minimal impact on the processes and equipment used for the manufacturing of such products due in part to the easier handling of such syrup.

The properties of low-viscosity reduced-sugar syrup of the present invention make the syrup particularly suitable in many food, beverage, and pharmaceutical applications. Non-limiting examples include as bulking, binding and coating ingredients for cereals, bars, confectioneries, beverages and sweet and savory products; carriers for coloring agents, flavors, fragrances and essences, and high potency sweeteners; spray drying adjuncts such as for coffee extracts and tea extracts; bulking, bodying and dispersing agents such as in synthetic creams or coffee whiteners; ingredients promoting a moisture retention in bread, pastry and meats; components of dry soup mixes, bakery mixes, frosting mixes, spice mixes and blends, coverage powders, condiments, gravy mixes, sauce mixes and frozen dairy foods, and in fat mimetics. In addition, they are useful in the formulation of tabulating compounds which can be used in food products or pharmaceutical products, anti-caking agents, whipped products, protective coatings, agglomeration aids, low or reduced-in-calorie foods and beverages.

Studies on the properties of the products of the low-viscosity reduced-sugar syrup of the present invention showed that the viscosities of the syrups were significantly decreased and the procedures of heating, concentration, mixing, etc., during the production of foods were greatly facilitated. Furthermore, the syrup of the present invention is less prone to discoloration due to its low level of reactive reducing sugars. The decrease in viscosity of the present invention was surprisingly more than expected and facilitated greatly the handling of the syrup. Furthermore, the sweetness of the present invention was surprisingly more than expected and facilitated greatly the desired sensory impression of finished foods and beverages with reduced sugars. In addition, the carbohydrate compositions of the present invention surprisingly retained more moisture compared to conventional carbohydrates containing similar (e.g., 36 DE) or higher (e.g., 43 DE) total mono- and di-saccharides (it is well known in the art that an increase in DE translates to an increase in capacity to absorb and/or retain moisture). With an increase in its capacity to retain moisture, the carbohydrate compositions extended the softness of foods containing such carbohydrate compositions (e.g., bars and soft candies) for a longer time, thereby extending the freshness and shelf-life of such foods. Irrelative to the increase in capacity of moisture retention, the carbohydrate compositions of the present invention yet exhibited moisture adsorption properties similar to 36DE and 43DE corn syrups. The moisture adsorption properties similar to a 36DE corn syrup and/or 43DE corn syrup is a surprising result because with not more than 25% total mono- and di-saccharides in the carbohydrate compositions of the present invention, the expectation would be that the moisture adsorption properties would be similar to a 28DE corn syrup. The relatively low hygroscopicity exhibited by the carbohydrate compositions of the present invention is useful in food applications, such as hard candies and cereal coatings, where high hygroscopicity is detrimental to such foods. Thus the superiority of the syrup of the present invention addresses the unmet need of manufacturers of food, beverage, and pharmaceutical products.

EXAMPLES

The following examples, including the materials and methods, are presented to illustrate the present invention and to assist one of ordinary skill in making and using the same. The examples are not intended in any way to otherwise limit the scope of the disclosure.

The Lane and Eynon method was used to measure the DE in Examples 3-6 and the commercial products in Tables 1-3 and 13. The DE values of the remaining examples were calculated using the reducing values of individual saccharides of DP1 to DP12 reported by Johnson and Srisuthep, "Physical and Chemical Properties of Oligosaccharides", Cereal Chemistry, 52(1): 70-78, 1975. A value of 0.05 was used for DP13 and greater. The reducing values of individual saccharides reported by Johnson and Srisuthep were determined using the Somogy method, which is similar to Lane and Eynon as described above.

Examples of Syrup and Methods of Preparing the Syrup

Although methods and materials similar or equivalent to those described herein can be used in the practice or testing of the present invention, suitable methods and materials are described below.

Example 1—Low-Viscosity Reduced-Sugar Syrup Sample #1

A starch slurry was made to about 45.8% DS, adjusted to about pH 1.8 with concentrated HCl and liquefied at about 260° F. to about a DE of 22. The liquefied starch liquor was cooled to about 145° F. and adjusted to about pH 5.1 with a NaOH solution. About 0.025% of a low-temperature alpha-amylase (Spezyme LT75, Genencor International, Rochester, N.Y.) and about 0.075% of a pullulanase (Optimax L-1000, Genencor), measured on a dry weight basis of starch, were added for saccharification at about 140° F. to about 150° F. for 46 hours with mild agitation.

The saccharified syrup then was heated to about 185° F. to inactivate the enzymes, filtered through the diatomaceous earth cake, passed through a granular activated carbon column at from about 160° F. to about 170° F., and evaporated at about 160° F. to a dry solid content of about 82.5%. The results of the DP and viscosity of the syrup product are shown in Tables 1 and 2. In addition a chromatograph showing the DP composition of this low-viscosity reduced-sugar syrup is shown in FIG. 1.

Example 2—Low-Viscosity Reduced-Sugar Syrup Sample #2

A starch slurry was made to about 46.1% DS, adjusted to about pH 1.8 with concentrated HCl and liquefied at about 260° F. to about a DE of 21. The liquefied starch liquor was cooled to about 145° F. and adjusted to a pH of about 5.0 with a NaOH solution. To the temperature- and pH-adjusted starch liquor, about 0.025% of a low-temperature alpha-amylase (Spezyme LT75, Genencor) and about 0.075% of a pullulanase (Optimax L-1000, Genencor), measured on a dry weight basis of starch, were added for saccharification at from about 140° F. to about 150° F. for 44 hours with mild agitation.

The saccharified syrup then was heated to about 185° F. to inactivate the enzymes, filtered through the diatomaceous earth cake, passed through a granular activated carbon column at from about 160° F. to about 170° F. and evaporated at about 160° F. to a DS of about 79%. The results of the DP and viscosity of the syrup product are shown in Tables 1 and 2.

Example 3—Low-Viscosity Reduced-Sugar Syrup Sample #3

A starch slurry was made to about 39.5% DS, adjusted to a pH of about 5.87 with soda ash and liquefied at about 215° F. in the presence of about 0.1% alpha amylase (Liquozyme Supra, Novozymes A/S, Bagsvaerd, Denmark) to a DE of about 13. The liquefied starch liquor was cooled to about 145° F. and adjusted to a pH of about 5.0 with a HCl solution. To the temperature- and pH-adjusted starch liquor, about 0.075% of a pullulanase (Optimax L-1000, Genencor), measured on a dry weight basis of starch, was added for saccharification at from about 140° F. to about 150° F. for about 43 hours with mild agitation.

The saccharified syrup then was heated to about 185° F. to inactivate the enzymes, filtered through the diatomaceous earth cake, passed through a granular activated carbon column at from about 160° F. to about 170° F. and evaporated at about 160° F. to a DS of about 77.8%. The results of the DP and viscosity of the syrup product are shown in Tables 1 and 2.

Example 4—Commercial-Scale Production of a Low-Viscosity Reduced-Sugar Syrup (Sample #4)

A starch slurry was acid-converted to a DE of about 26, a DS of about 45.9%, and a pH of about 4.9, and then cooled to about 145° F. to about 150° F. About 0.002% of an alpha-amylase (BAN 480, Novo Nordisk, Denmark) and about 0.1% of a pullulanase (Optimax L-1000, Genencor), measured on a dry weight basis of starch, were added for saccharification at from about 145° F. to about 150° F. for 16 hours with mild agitation. Saccharification was carried out in vessels that each contained about 45,000 gallons of starch slurry. The saccharified syrup then was adjusted to a pH of from about 3.0 to about 3.3 with a HCl solution to deactivate the enzymes, passed through a granular activated carbon column at about 160° F. and evaporated to a DS of about 79.0%. The results of the DP and viscosity of the syrup product are shown in Tables 1 and 2.

Example 5—DP and Viscosity of Low-Viscosity Reduced-Sugar Syrup Compared to Commercially Available Syrup Products As shown in Table 1, the low-viscosity reduced-sugar syrup of the present invention exhibited a unique carbohydrate profile not seen in the commercially available syrup. The low-viscosity reduced-sugar syrup of the present invention is characterized by its lower concentrations of DP1 and DP2 and higher concentrations of DP3, DP5 and DP6 as compared to the commercially available syrup product having similar total mono- and di-saccharides. The low-viscosity reduced-sugar syrup described herein also contained significantly lower amounts of higher saccharides, particularly DP15+ as compared to conventional corn syrup product having a similar total mono- and di-saccharides or a similar DE.

TABLE 1

| | DE | DP1 | DP2 | DP3 | DP4 | DP5 | DP6 | DP7 | DP8+ | (DP15+) |
|---|---|---|---|---|---|---|---|---|---|---|
| *DP profile (% on total carbohydrate basis)* | | | | | | | | | | |
| *Low-viscosity reduced sugar syrup* | | | | | | | | | | |
| #1 | 29 | 7 | 11 | 13 | 9 | 11 | 17 | 8 | 24 | (8) |
| #2 | 32 | 6 | 10 | 13 | 9 | 11 | 17 | 8 | 26 | (9) |
| #3 | 29 | 2 | 11 | 15 | 7 | 17 | 20 | 5 | 23 | (15) |
| #4 | 31 | 8 | 9 | 12 | 8 | 9 | 15 | 9 | 30 | (12) |
| *Specialty syrup products* | | | | | | | | | | |
| Fuji Oligo G67 | 26 | 4 | 14 | 7 | 7 | 9 | 20 | 20 | 19 | NA |
| Fuji Oligo #360 | 27 | 7 | 19 | 60 | 6 | 2 | 3 | 1 | 2 | NA |
| Fuji Oligo #450 | 43 | 2 | 7 | 9 | 50 | 3 | 3 | 3 | 23 | NA |
| Fuji Oligo #470 | NA | 2 | 7 | 10 | 72 | 0 | 1 | 0 | 8 | NA |
| *Conventional corn syrup solids* | | | | | | | | | | |
| 21DE (C*1920) | 21 | 2 | 8 | 9 | 4 | 9 | 13 | 4 | 51 | (45) |
| 25DE (C*1925) | 25 | 3 | 10 | 12 | 6 | 11 | 19 | 5 | 34 | (30) |
| 40 DE (C*1987) | 40 | 3 | 29 | 44 | 1 | 2 | 2 | 1 | 18 | (16) |
| *Conventional corn syrup products* | | | | | | | | | | |
| 25 DE | 25 | 6 | 7 | 10 | 7 | 7 | 11 | 10 | 42 | (30) |
| 28 DE | 28 | 7 | 9 | 11 | 7 | 8 | 12 | 11 | 38 | (27) |
| 36 DE | 36 | 16 | 11 | 12 | 10 | 8 | 8 | 6 | 30 | (24) |
| 43 DE | 43 | 20 | 15 | 12 | 8 | 7 | 7 | 5 | 26 | (20) |
| 63 DE | 63 | 35 | 29 | 9 | 6 | 5 | 4 | 3 | 11 | (6) |

*Fuji Oligo syrups are products of Nihon Shokuhin Kako Kogyo Kabushiki Kasha of Japan (Tokyo, Japan); for these samples, DP15+ was included in DP8+.
**The conventional 25-63DE products are commercially available from Cargill (Wayzata, MN).
NA = not available.

Another unique characteristic of the syrup described herein is its low viscosity. As shown in Table 2, at similar DS and DE levels, the syrup of the present invention exhibited significantly lower viscosity (from about 40% to about 50% lower) across a wide range of temperatures than the viscosity of conventional syrup products.

TABLE 2

Viscosity (Cps) of low-viscosity reduced sugar syrup compared with conventional corn syrup products

| | Conventional syrup products | | | | | Low-viscosity reduced-sugar syrup sample | | | |
|---|---|---|---|---|---|---|---|---|---|
| | | | | | | #1 | #2 | #3 | #4 |
| DE | 25DE | 28DE | 36DE | 43DE | 63DE | 29DE | 32DE | 29DE | 31DE |
| % DS | 78.2 | 78.3 | 80.4 | 80.7 | 82.0 | 82.5 | 79 | 77.8 | 79.0 |
| 110° F. | 23000 | 23000 | 18500 | 11000 | 4000 | 10750 | 6470 | 12350 | 10990 |
| 120° F. | 13000 | 13000 | 8700 | 7000 | 2500 | 5900 | 3680 | 7350 | 7310 |
| 140° F. | 5000 | 5000 | 3100 | 2500 | 1000 | 2040 | <2000 | 3048 | 2100 |

It is readily seen from Table 3 that the syrups of the present invention provide unique carbohydrate composition having total mono- and di-saccharides of less than about 25%, oligosaccharides of DP3 to DP10 greater than about 50%, oligosaccharides of DP3 to DP14 greater than about 60%, and polysaccharides less than about 15%, resulting in First Oligosaccharide Index of greater than about 2.0 and Second Oligosaccharide Index greater than about 3.0. In comparison, the conventional syrup products contain more than about 20% polysaccharides with First Oligosaccharide Index of less than about 2.0 and Second Oligosaccharide Index less than about 2.0. It is also readily seen from Table 3 that syrups of the present invention exhibit significantly lower, from about 30% to about 90% lower, viscosities across a wide temperature range at 78% DS than the conventional syrups having similar total mono- and di-saccharides.

national, Rochester, N.Y.), measured on a dry weight basis of starch, was added for saccharification at from about 145° F. to about 150° F. for 43 hours with mild agitation. The saccharified syrup was then heated to about 185° F. to deactivate the enzymes, filtered through the diatomaceous earth cake, passed through a granular activated carbon column at about 160° F. and evaporated to 80.3% DS. The results of the carbohydrate composition of the final syrup product are shown in Table 4. Compared to the conventional syrup with similar total mono- and di-saccharides and DE, syrups #5 and #6 of the present invention showed a unique DP particularly enriched in oligosaccharides of DP3-DP10 and DP3-DP 14, resulting in First Oligosaccharide Index of greater than about 2.0 and Second Oligosaccharide Index of greater than about 3.0.

TABLE 3

As compared to a current commercial syrup product having similar total mono- and disaccharides (DP1 + DP2) and DE values, syrups of this invention exhibited vary different carbohydrate composition and significantly lower viscosities.

| | | carbohydrate composition | | | | | | viscosity (cPs) at 78% DS | | |
|---|---|---|---|---|---|---|---|---|---|---|
| | DE | DP1 + DP2 | DP3-7 | DP3-10 | DP3-14 | DP15+ | oligosaccharide Index-I | oligosaccharide Index-II | 100° F. | 120° F. | 140° F. |
| syrup#1 | 29 | 18 | 58 | 68 | 74 | 8 | 4.7 | 9.3 | 3,220 | 1,210 | 527 |
| syrup#2 | 32 | 16 | 58 | 68 | 74 | 9 | 4.3 | 7.9 | 7,470 | 2,670 | 1,100 |
| syrup#3 | 29 | 13 | 64 | 70 | 73 | 15 | 3.9 | 4.9 | 23,900 | 7,950 | 3,090 |
| syrup#4 | 31 | 17 | 53 | 62 | 71 | 12 | 3.0 | 6.2 | 12,500 | 4,320 | 1,740 |
| 28DE CSU | 28 | 16 | 49 | 56 | 56 | 28 | 2.0 | 2.0 | 35,700 | 11,600 | 4,410 |

Example 6—Low-Viscosity Reduced-Sugar Syrup Sample #5

A starch slurry was made to about 36.9% DS, adjusted to a pH of about 6.0 with soda ash and liquefied at about 215° F. in the presence of about 0.1% Liquozyme Supra (Novozymes A/S, Bagsvaerd, Denmark) to a DE of about 15.1. The liquefied liquor was then cooled to about 145° F., adjusted to a pH of about 4.5 with HCl solution, and about 0.1% of a pullulanase (Optimax L-1000, Genencor International, Rochester, N.Y.), measured on a dry weight basis of starch, was added for saccharification at from about 145° F. to about 153° F. for about 28 hours with mild agitation. The saccharified syrup was then heated to about 185° F. to deactivate the enzymes, filtered through the diatomaceous earth cake, passed through a granular activated carbon column at about 160° F. and evaporated to about 78.0% DS. The results of the carbohydrate composition are shown in Table 4.

Example 7—Low-Viscosity Reduced-Sugar Syrup Sample #6

A starch slurry was made to about 36.7% DS, adjusted to a pH of about 5.9 with soda ash and liquefied at about 215° F. in the presence of about 0.1% Liquozyme Supra (Novozymes A/S, Bagsvaerd, Denmark) to a DE of about 13.0. The liquefied liquor was then cooled to about 145° F., adjusted to a pH of about 4.5 with HCl solution, and about 0.075% of a pullulanase (Optimax L-1000, Genencor Inter-

TABLE 4

DP profile of syrup products given in Examples 6 & 7

| DP | Syrup #5 | Syrup #6 | 28DE CSU |
|---|---|---|---|
| DP1 | 2.3 | 2.2 | 7.1 |
| DP2 | 11.1 | 11.2 | 8.6 |
| DP3 | 15.6 | 15.8 | 10.9 |
| DP4 | 7.3 | 7.2 | 7.0 |
| DP5 | 17.6 | 17.7 | 7.7 |
| DP6 | 21.3 | 21.0 | 12.0 |
| DP7 | 4.2 | 4.1 | 11.2 |
| DP8 | 2.6 | 2.4 | 4.3 |
| DP9 | 2.1 | 2.1 | 3.2 |
| DP10 | 0.0 | 1.5 | |
| DP11 | 1.4 | 3.3 | |
| DP12 | 3.3 | 0.0 | |
| DP13 | 0.0 | 0.0 | |
| DP14 | 0.0 | 0.0 | |
| DP15+ | 11.1 | 11.5 | 28.0 |
| DP1 + 2 | 13.5 | 13.4 | 15.7 |
| DP3-7 | 66.0 | 65.9 | 48.8 |
| DP3-10 | 70.7 | 71.8 | 56.3 |
| DP3-14 | 75.4 | 75.1 | 56.3 |
| Oligosaccharide index-I | 4.5 | 4.9 | 2.0 |
| Oligosaccharide index-II | 6.8 | 6.5 | 2.0 |
| DE | 27 | 27 | 28 |

Example 8—Low-Viscosity Reduced-Sugar Syrup

An acid liquefied starch slurry of about 20 to about 26 DE was obtained from a Cargill Corn Milling plant. After the liquefied starch slurry was cooled to about 150° F., it was adjusted with a HCl solution or a NaOH solution to about pH 4.8. An isoamylase (Hayashibara, Okayama, Japan) or a pullulanase (Optimax L-1000, Genencor International, Rochester, N.Y., USA) in combination with an alpha-amylase (BAN 480, Novo Nordisk, Denmark) were added at various dosages (from about 0.002% to about 0.4% on starch dry weight basis) and reacted for from about 6 to about 32 hours. The resulting syrup had less than about 18% total mono- and di-saccharides, at least about 60% of DP3-DP10, at least about 70% of DP3-DP14 and no more than about 12% of DP15 or higher as shown in the Table 5. As compared to the conventional syrup having similar total mono- and disaccharides and DE, syrups A through E had First Oligosaccharide Index of greater than about 2.0 and Second Oligosaccharide Index greater than about 3.0, and exhibited substantially lower viscosities from about 60% to about 97% lower.

milling plant. After the liquefied starch slurry was cooled to about 140° F., it was adjusted with a HCl solution to a pH of about 4.5. An isoamylase (Hayashibara, Okayama, Japan), alone or in combination with a pullulanase (Optimax L-1000, Genencor International, Rochester, N.Y.), was added at various dosages from about 0.2% to about 0.7% on starch dry weight basis and reacted at about 110° F. to about 150° F. for about 6 to about 44 hours. The resulting syrup had less than about 12% total mono- and di-saccharides, at least about 70% of DP3 to DP10, at least about 80% of DP3 to DP14, and no more than about 8% of DP15 or higher as shown in Table 6. Syrups A through E exhibited substantially lower viscosities (from about 40% to about 73%

TABLE 5

DP profiles and viscosities of syrup products in Example 8 as compared to the conventioanl syrup.

|  | A | B | C | D | E | 28DE CSU |
|---|---|---|---|---|---|---|
| Reaction conditions | | | | | | |
| pH | 4.8 | 4.7 | 4.8 | 4.8 | 4.8 | |
| Temperature (° F.) | 148 | 149 | 122 | 149 | 149 | |
| Time (Hr) | 16 | 32 | 6 | 22 | 22 | |
| Enzyme dosage, % on starch dry solids | | | | | | |
| Isoamylase | — | — | 0.4 | — | 0.4 | |
| Optimax L1000 | 0.1 | 0.3 | — | 0.4 | — | |
| BAN 480 | 0.002 | 0.002 | 0.1 | 0.01 | 0.01 | |
| Profile | | | | | | |
| DP1 | 7.6 | 5.6 | 6.7 | 6.5 | 6.4 | 7.1 |
| DP2 | 9.4 | 8.3 | 11.2 | 10.7 | 10.6 | 8.6 |
| DP3 | 11.8 | 11.6 | 14.0 | 13.7 | 13.1 | 10.9 |
| DP4 | 8.4 | 9.2 | 9.9 | 9.9 | 9.5 | 7.0 |
| DP5 | 9.4 | 9.1 | 13.2 | 11.0 | 10.6 | 7.7 |
| DP6 | 14.6 | 14.0 | 17.3 | 16.6 | 17.6 | 12.0 |
| DP7 | 9.2 | 11.8 | 5.6 | 10.2 | 10.7 | 11.2 |
| DP8 | 3.8 | 5.9 | 0.0 | 0.0 | 0.0 | 4.3 |
| DP9 | 3.1 | 4.5 | 3.1 | 3.7 | 3.7 | 3.2 |
| DP10 | 2.1 | 3.2 | 3.2 | 3.5 | 3.7 | |
| DP11 | 2.0 | 2.5 | 2.5 | 2.8 | 2.9 | |
| DP12 | 6.9 | 2.9 | 2.3 | 2.3 | 2.3 | |
| DP13 | 0.0 | 3.2 | 1.5 | 2.1 | 9.0 | |
| DP14 | 0.0 | 0.4 | 2.0 | 3.6 | 0.0 | |
| DP15+ | 11.6 | 7.9 | 7.5 | 3.5 | 0.0 | 28.0 |
| DP1 + 2 | 17.0 | 13.9 | 17.9 | 17.2 | 17.0 | 15.7 |
| DP3-10 | 62.4 | 69.2 | 66.3 | 68.6 | 68.8 | 56.3 |
| DP3-14 | 71.4 | 78.2 | 74.6 | 79.3 | 83.0 | 56.3 |
| Oligosaccharide index-I | 3.0 | 4.1 | 4.2 | 4.8 | 4.9 | 2.0 |
| Oligosaccharide index-II | 6.2 | 9.9 | 9.9 | 22.5 | >100 | 2.0 |
| DE | 29 | 27 | 30 | 30 | 30 | 28 |
| Viscosity @78% DS, 100° F. | 15,600 | 12,500 | 3,500 | 3,500 | 3,000 | 40,000 |

Example 9—Low-Viscosity Reduced-Sugar Syrup

Corn starch slurry, liquefied with about 0.1% of Liquozyme Supra (Novozymes A/S, Bagsvaerd, Denmark) to about 12 to about 14 DE, was obtained from a Cargill corn lower) compared to the conventional syrup having similar total mono- and disaccharides and DE. In addition, First Oligosaccharide Index of greater than about 2.0 and Second Oligosaccharide Index of greater than about 3.0 were obtained.

TABLE 6

DP profiles and viscosities of syrup products in Example 9 as compared to the conventional syrup.

|  | A | B | C | D | E | 25DE CSU |
|---|---|---|---|---|---|---|
| Reaction conditions | | | | | | |
| pH | 4.5 | 4.7 | 4.5 | 4.5 | 4.5 | |
| Temperature (° F.) | 113 | 149 | 122 | 138 | 140 | |
| Time (Hr) | 44 | 6 | 26 | 26 | 16 | |
| Enzyme dosage, % on | | | | | | |

TABLE 6-continued

DP profiles and viscosities of syrup products in Example 9 as compared to the conventional syrup.

|  | A | B | C | D | E | 25DE CSU |
|---|---|---|---|---|---|---|
| starch dry solids |  |  |  |  |  |  |
| Isoamylase | 0.6 | 0.4 | 0.7 | 0.4 | 0.2 |  |
| Optimax L1000 | — | — | — | 0.3 | 0.4 |  |
| Profile |  |  |  |  |  |  |
| DP1 | 1.1 | 1.7 | 0.2 | 1.4 | 1.6 | 6.0 |
| DP2 | 8.1 | 9.0 | 8.8 | 8.8 | 9.7 | 7.4 |
| DP3 | 16.5 | 16.3 | 17.7 | 17.2 | 18.1 | 9.6 |
| DP4 | 6.8 | 7.3 | 8.3 | 8.1 | 8.3 | 7.0 |
| DP5 | 12.1 | 12.3 | 13.2 | 12.4 | 14.4 | 7.3 |
| DP6 | 19.6 | 21.2 | 21.1 | 19.3 | 19.6 | 10.8 |
| DP7 | 12.5 | 12.5 | 15.7 | 12.6 | 10.4 | 10.0 |
| DP8 | 3.2 | 2.1 | 0.0 | 3.1 | 1.9 | 3.8 |
| DP9 | 4.5 | 1.0 | 1.2 | 1.4 | 1.6 | 3.4 |
| DP10 | 2.4 | 2.3 | 3.2 | 3.3 | 2.5 | 2.5 |
| DP11 | 2.0 | 1.8 | 2.2 | 2.3 | 1.8 | 2.1 |
| DP12 | 1.5 | 1.2 | 0.0 | 1.7 | 1.6 |  |
| DP13 | 2.5 | 3.5 | 8.4 | 7.2 | 3.2 |  |
| DP14 | 1.4 | 0.0 | 0.0 | 0.0 | 0.0 |  |
| DP15+ | 5.8 | 7.7 | 0.0 | 1.2 | 5.3 | 30.1 |
| DP1 + 2 | 9.1 | 10.7 | 9.0 | 10.3 | 11.3 | 13.4 |
| DP3-10 | 77.7 | 75.1 | 80.5 | 77.3 | 76.8 | 54.4 |
| DP3-14 | 85.1 | 81.6 | 91.0 | 88.6 | 83.4 | 56.6 |
| Oligosaccharide index-I | 5.9 | 5.3 | 7.6 | 6.2 | 6.4 | 1.7 |
| Oligosaccharide index-II | 14.6 | 10.6 | >100 | 75.7 | 15.6 | 1.9 |
| DE | 25 | 26 | 25 | 26 | 27 | 25 |
| Viscosity @78% DS, 100° F. | 17,400 | 24,000 |  | 11,200 | 11,000 | 40,000 |

Example 10—Low-Viscosity Reduced-Sugar Syrup

Corn starch slurry, liquefied with about 0.1% of Liquozyme Supra (Novozymes A/S, Bagsvaerd, Denmark) to a DE of about 12 to about 14, was obtained from a Cargill corn milling plant. After the liquefied starch slurry was cooled to about 140° F., it was adjusted either with a NaOH or a HCl solution to about a pH of about 5.8. An amylase (AMT 1.2 L, Amano Enzyme, Nagoya, Japan) and a debranching enzyme (Kleistase PL45, Daiwa Kasei, Shiga, Japan), or in combination with another amylase (Fuelzyme-LF, Verenium, San Diego, Calif.), were added at various dosages (from about 0.005% to about 0.4% on starch dry weight basis) and reacted at about 135° F. to about 140° F. for about 20 hours to about 30 hours. A portion of syrup-D was further treated with about 1.2% (w/v) of distillers active dry yeast (SuperStart, a product of Lallemand Ethanol Technology, Chicago, Ill.) and about 1% of urea at about 110° F. to about 115° F. until the mono- and disaccharides were substantially consumed (syrup-F). The resulting syrup had about 8% to about 22% of total mono and di-saccharides, 45-53% of DP3, more than 55% DP3 and DP4, at least about 60% of DP3-DP10, at least about 70% of DP3-DP14 and no more than about 10% of DP15 or higher as shown in Table 7. The syrups had unique saccharide compositional profiles with DP2/DP5 ratios of about 2 to 6, DP3/DP5 ratios of about 10 to 16 and DP(3+4)/DP5 ratios of about 13-18, and theoretical sweetness of about 24 to about 29. Syrups A through F exhibited substantially lower viscosities (from about 54% to about 59% lower) compared to the conventional syrup having similar total mono- and disaccharides and DE. In addition, First Oligosaccharide Index of greater than about 2.0 and Second Oligosaccharide Index of greater than about 3.0 were obtained.

TABLE 7

DP profiles and Viscosities of syrup products in Example 10 as compared to the conventional syrup.

|  | A | B | C | D | E | F | 36DE CSU |
|---|---|---|---|---|---|---|---|
| Reaction conditions |  |  |  |  |  |  |  |
| pH | 5.8 | 5.8 | 5.8 | 5.8 | 5.8 |  |  |
| Temperature (° F.) | 140 | 136 | 137 | 137 | 140 |  |  |
| Time (Hr) | 30 | 28 | 26 | 21 | 28 |  |  |
| Enzyme dosage, % on starch dry solids |  |  |  |  |  |  |  |
| Fuelzyme LF | — | — | 0.0075 | 0.01 | 0.005 |  |  |
| AMT 1.2L | 0.4 | 0.4 | 0.4 | 0.4 | 0.4 |  |  |
| Kleistase PL45 | 0.4 | 0.4 | 0.4 | 0.4 | 0.3 |  |  |

TABLE 7-continued

DP profiles and Viscosities of syrup products in Example 10 as compared to the conventional syrup.

| Profile | A | B | C | D | E | F | 36DE CSU |
|---|---|---|---|---|---|---|---|
| DP1 | 3.3 | 2.8 | 3.5 | 3.0 | 3.1 | 0.2 | 16.1 |
| DP2 | 19.2 | 18.5 | 18.6 | 17.9 | 18.0 | 7.6 | 10.5 |
| DP3 | 48.7 | 47.4 | 46.6 | 44.8 | 48.5 | 53.4 | 12.4 |
| DP4 | 8.2 | 8.1 | 9.7 | 10.8 | 8.7 | 12.3 | 10.4 |
| DP5 | 3.1 | 3.2 | 4.1 | 4.3 | 3.5 | 4.1 | 8.2 |
| DP6 | 5.5 | 7.3 | 6.5 | 7.2 | 6.1 | 2.3 | 8.2 |
| DP7 | 1.8 | 1.8 | 2.6 | 2.8 | 2.3 | 8.5 | 6.4 |
| DP8 | 0.8 | 0.0 | 0.0 | 0.0 | 1.4 | 3.0 | 3.2 |
| DP9 | 0.8 | 1.0 | 1.6 | 1.9 | 1.3 | 2.1 | 2.3 |
| DP10 | 0.4 | 1.0 | 1.4 | 1.7 | 0.8 | 1.7 | 2.1 |
| DP11 | 0.2 | 0.3 | 0.9 | 1.1 | 0.6 | 0.9 | 1.4 |
| DP12 | 0.2 | 0.0 | 0.6 | 0.8 | 0.8 | 0.7 | |
| DP13 | 0.2 | 0.0 | 0.9 | 0.7 | 0.0 | 0.6 | |
| DP14 | 0.0 | 0.0 | 0.2 | 1.2 | 0.0 | 1.1 | |
| DP15+ | 7.6 | 8.6 | 2.7 | 2.0 | 5.0 | 1.5 | 18.8 |
| DP1 + 2 | 22.5 | 21.3 | 22.1 | 20.9 | 21.1 | 7.7 | 26.6 |
| DP3-4 | 56.9 | 55.5 | 56.3 | 55.7 | 57.2 | 65.7 | 22.8 |
| DP3-10 | 69.3 | 69.8 | 72.6 | 73.4 | 72.6 | 87.5 | 53.2 |
| DP3-14 | 69.9 | 70.1 | 75.2 | 77.1 | 73.9 | 90.8 | 54.6 |
| Oligosaccharide Index-I | 8.5 | 7.8 | 13.7 | 13.0 | 11.4 | 18.2 | 2.6 |
| Oligosaccharide index-II | 9.2 | 8.1 | >100 | 38.4 | 14.9 | 60.5 | 2.9 |
| DE | 37 | 36 | 38 | 37 | 37 | 32 | 36 |
| Viscosity @78% DS, 100° F. | 9,300 | | | 8,200 | 8,300 | 9,500 | 20,000 |
| DP2/DP5 | 6.2 | 5.8 | 4.5 | 4.2 | 5.2 | 1.9 | 1.3 |
| DP3/DP5 | 15.8 | 14.8 | 11.3 | 10.4 | 13.9 | 13.1 | 1.5 |
| DP(3 + 4)/DP5 | 18.42 | 17.33 | 13.60 | 12.94 | 16.43 | 16.11 | 2.78 |
| Theoretical sweetness | 28.8 | 27.9 | 28.6 | 27.7 | 28.3 | 23.9 | 25.6 |

Example 11—Low-Viscosity Reduced-Sugar Syrup

Regular dent corn starch slurry, liquefied with about 0.1% of Liquozyme Supra (an amylase product of Novozymes A/S, Bagsvaerd, Denmark) to a DE of about 12 to about 14, was obtained from a Cargill corn milling plant. After the liquefied starch slurry was cooled to about 145° F. and adjusted with a HCl solution to a pH of about 4.6, Optimax L-1000 (a pullulanase product of Genencor International, Rochester, N.Y., USA) and GrindAmyl (an amylase product of Danisco A/S, Copenhagen, Denmark) were added at dosages of about 0.4% and about 0.2% respectively on starch dry weight basis and reacted at about 144° F. to about 150° F. for about 18 hours. The resulting syrups were subjected to two treatments. In one treatment, a portion of the syrup was filtered through diatomaceous earth to remove impurities (e.g., protein, fiber, lipids, etc.) and decolored by passing through an activated carbon column, then concentrated in a rotary evaporator to a final solid concentration of about 80.6% DS (A). In the other treatment, another portion of the syrup, after filtered through diatomaceous earth and decolored through activated carbon, was treated with about 1.2% (w/v) of distillers active dry yeast (SuperStart, a product of Lallemand Ethanol Technology, Chicago, Ill.) and about 1% urea at about 110° F. to about 115° F. until all mono- and di-saccharides were consumed. The reaction mixture was filtered to remove yeast cells and then subjected to decolorization through an activated carbon column. The decolored syrup was either evaporated to a final solid concentration of about 80.5% DS (B), or filtered through a membrane with about 3K molecule weight cut-off, then evaporated to a final solid concentration of about 79.9% DS (C). As shown in Table 8, syrups 8A through 8C contained very high levels of DP4 with total DP3+DP4 exceeding about 60%. Syrups 8A through 8C were also very low in DP15+ (less than about 6%) with syrup-8C containing less than about 2% DP2, only about 0.2% DP15+ and devoid of DP1. Syrups 8A through 8C also showed unique saccharide profiles with DP2/DP5 ratios of 4.7-7.1, DP3/DP5 ratios of 9.3-13.9, DP(3+4)/DP5 ratios of 10.3-14.5, and theoretical sweetness of 19.7-27.5. Syrups 8A through 8C exhibited First Oligosaccharide Index of greater than about 2.0 and Second Oligosaccharide Index of greater than about 3.0, whereas for conventional syrups having similar DE, the First Oligosaccharide Index was only about 2.0 for a 28 DE syrup and up to about 2.9 for a 36 DE syrup. As compared to the conventional syrups having similar DE, syrups 8A through 8C had significantly higher DP2/DP5, DP3/DP5 and DP(3+4)/DP5 ratios. As compared to the conventional syrup having similar DE values, syrups 8A through 8C also exhibited significantly lower viscosities. For example Syrup-8A, which had similar DE and less total mono- and di-saccharide than a conventional 36 DE syrup, exhibited about 60% lower viscosity than a conventional 36 DE syrup. With the same DE value, Syrup-8B contained only about 2% total mono- and di-saccharides as compared to about 16% total mono- and di-saccharides for a conventional 28 DE syrup. Syrup-8B also exhibited about 30% lower viscosity than a conventional 28 DE syrup.

TABLE 8

DP profile and viscosity of syrup products of Example 11 as compared to conventional syrups

| Profile | A | B | C | 28DE CS | 36DE CS |
|---|---|---|---|---|---|
| DP1 | 8.3 | 0.0 | 0.0 | 7.1 | 16.1 |
| DP2 | 14.5 | 2.0 | 1.7 | 8.6 | 10.5 |
| DP3 | 20.2 | 23.8 | 26.3 | 10.9 | 12.4 |
| DP4 | 39.6 | 49.1 | 54.2 | 7.0 | 10.4 |
| DP5 | 1.6 | 3.1 | 2.8 | 7.7 | 8.2 |
| DP6 | 2.8 | 5.0 | 4.6 | 12.0 | 8.2 |
| DP7 | | 0.0 | 0.0 | 11.2 | 6.4 |

TABLE 8-continued

DP profile and viscosity of syrup products of Example 11 as compared to conventional syrups

| Profile | A | B | C | 28DE CS | 36DE CS |
|---|---|---|---|---|---|
| DP8 | 2.9 | 4.2 | 4.0 | 4.3 | 3.2 |
| DP9 | 3.1 | 4.1 | 3.9 | 3.2 | 2.3 |
| DP10 | 0.4 | 0.7 | 0.5 | | 2.1 |
| DP11 | 0.5 | 0.8 | 0.6 | | 1.4 |
| DP12 | 0.8 | 1.5 | 1.2 | | |
| DP13 | 0.0 | 0.0 | 0.0 | | |
| DP14 | 0.0 | 0.0 | 0.0 | | |
| DP15+ | 5.3 | 5.6 | 0.2 | 28.0 | 18.8 |
| DP1 + 2 | 22.8 | 2.0 | 1.7 | 15.7 | 26.6 |
| DP3-4 | 59.8 | 72.9 | 80.5 | 17.9 | 22.8 |
| DP3-7 | 64.3 | 81.0 | 87.9 | 48.8 | 45.6 |
| DP3-10 | 70.6 | 90.1 | 96.3 | 56.3 | 53.2 |
| DP3-14 | 71.9 | 92.4 | 98.1 | 56.3 | 54.6 |
| Oligosaccharide Index-I | 10.7 | 11.4 | 49.6 | 2.0 | 2.6 |
| Oligosaccharide index-II | 13.6 | 16.6 | 632.1 | 2.0 | 2.9 |
| DE | 38 | 28 | 30 | 28 | 36 |
| Viscosity @78% DS, 100° F. | 7,800 | 28,000 | 9,750 | 40,000 | 20,000 |
| DP2/DP5 | 7.1 | 4.7 | 5.7 | 0.9 | 1.5 |
| DP3/DP5 | 13.9 | 9.7 | 11.8 | 0.6 | 1.3 |
| DP(3 + 4)/DP5 | 14.51 | 10.34 | 12.43 | 1.23 | 2.27 |
| Theoretical sweetness | 27.5 | 19.7 | 20.9 | 18.2 | 25.6 |

Example 11A-1—Sweetness of Syrup-8A

Syrup A from Table 8 ("Syrup-8A") was evaluated for sweetness. Two solutions of Syrup-8A were made to 15% solids, one using the Refractive Index Dry Substance (RI-DS), Standard Analytical Method E-54 (Corn Refiners Association, 6$^{th}$ Edition, 1977, E-54, pp. 1-11) data (18.7 g solids; 81.3 mL water) ("COA"), and one using refractometer data (18.2 g solids; 81.8 mL water). Samples were provided as 1.5 oz samples in a 2 oz cup, at room temperature.

A total of 7 Quantitative Descriptive Analysis ("QDA") taste panelists trained with sucrose, and were then provided with two samples each of the COA and refractometer samples, and evaluated on a scale of 0-100, with 0 having no sweetness and 100 having sweetness equivalent to sucrose. The results are shown in Table 8A-1, which shows that Syrup-8A has an average relative sweetness of 44 to 46.

TABLE 8A-1

Sweetness of Syrup-8A

| Sample | Sweetness Score Average | Replication 1 | Replication 2 |
|---|---|---|---|
| COA | 46 | 45 | 47 |
| Refractometer | 44 | 42 | 45 |

Example 11A-2—Relative Sweetness of Syrup-8A

Syrup-8A was also evaluated for sweetness relative to two corn syrups with known sweetness, 36DE (sweetness 30-40, 15% solution) and 43DE corn syrups (sweetness 40-50, 15% solution). Two solutions of Syrup-8A, and one solution each of Cleardex® 36/43 and Clearsweet® 43/43 IX, were each made to 15% solids. Samples were provided as approximately 1 oz samples in a 2 oz cup, at room temperature.

Two forced-choice paired comparison tests were separately conducted between Syrup-8A and Cleardex® 36/43 (Test (a)), and Syrup-8A and Clearsweet® 43/43 IX (Test (b)), where panelists were instructed to choose the sweeter sample in each test. Panelists were instructed to rinse well with water before tasting the samples, and were allowed to re-taste, as necessary. The results of these tests are shown in Tables 8A-1(a) and 8A-1(b).

TABLE 8A-1(a)

Results of Test (a) Comparing Sweetness of Syrup-8A to Cleardex ® 36/43

| Sample | Number of Panelists Indicated Sweeter | % Panelists |
|---|---|---|
| Syrup-8A | 56 | 76 |
| Cleardex ® 36/43 | 18 | 24 |

TABLE 8A-1(b)

Results of Test (a) Comparing Sweetness of Syrup-8A to Clearsweet ® 43/43 IX

| Sample | Number of Panelists Indicated Sweeter | % Panelists |
|---|---|---|
| Syrup-8A | 38 | 49 |
| Clearsweet ® 43/43 IX | 39 | 51 |

As seen in Table 8A-1(a), approximately three times more panelists concluded that Syrup-8A was sweeter than the Cleardex® 36/43. However, as seen in Table 8A-1(b), approximately the same number of panelists concluded that the Clearsweet® 43/43 IX and Syrup-8A were similarly sweet. These results demonstrate that Syrup-8A has sweetness that is approximately equivalent to a 43DE corn syrup, which is known to have a sweetness of about 40-50 relative to sucrose.

As shown in Table 8A-1(c), at similar sugar levels, Syrup-8A is about 29% sweeter than regular corn syrup Cleardex® 36/43. At similar sweetness levels, Syrup-8A of the present invention contains about 30% less sugar than regular corn syrup Clearsweet® 43/43. This data clearly demonstrates that Syrup-8A meets a previously unmet need for reducing sugar without reducing sweetness.

TABLE 8A-1(c)

Sugar (total DP1 + DP2) and sweetness of Syrup-8A in comparison with regular corn syrups

| Product | Sugar | | Sweetness | |
| | % Total DP1 + DP2 | Difference | Sweetness | Difference |
|---|---|---|---|---|
| Syrup-8A | 23 | | 45 | |
| Cleardex ® 36/43 | 25 | −8% | 35 | +29% |
| Clearsweet ® 43/43 | 33 | −30% | 45 | Equal |

Example 11B—Calculation of Theoretical Sweetness of Syrup-8A

Table 8B shows the theoretical calculated sweetness values for Syrup-8A as well as a 43DE corn syrup. Additionally, the theoretical sweetness for other reported compositions is also calculated.

Example 11C—DP2/DP5, DP3/DP5 and (DP3+4)/DP5 ratios of Syrup-8A

As seen in Table 8B, Syrup-8A has surprisingly higher DP2/DP5, DP3/DP5 and (DP3+4)/DP5 ratios as compared to Clearsweet 43/43, as well as those also having 30% or more of DP4. It is postulated that these unique ratios may also have contributed to the surprisingly sweet sensory of the syrups of present invention.

TABLE 8B

Calculated Sweetness, DP2/DP5, DP3/DP5 and (DP3 + 4)/DP5 ratios

|  | Sweetness | Syrup-8A | 43 DE CS | Fuji-oligo[2] #450 | Fuji-oligo[2] #470 | JPS5817049 2 Table 1 | JPS5817049 2 #3 | U.S. Pat. No. 3,654,082 Table VIII | US20130197104, Table 4 |
|---|---|---|---|---|---|---|---|---|---|
| Calculated Sweetness |  | 27 | 29 | 19 | 22 | 24 | 26 | 24 | 23 |
| DP1[1] | 70 | 8.27 | 17.6 | 2 | 2 | 4.1 | 4 | 2.7 | 3.95 |
| DP2 | 45 | 14.51 | 17.27 | 7 | 7 | 13 | 16.8 | 7.8 | 14.08 |
| DP3 | 30 | 20.23 | 12.16 | 9 | 10 | 13.8 | 15.9 | 11.7 | 14.02 |
| DP4 | 20 | 39.61 | 7.77 | 50 | 72 | 36.2 | 34.2 | 63.4 | 41.66 |
| DP5 | 15 | 1.61 | 6.96 | 3 | 0 | 20.7 | 22.9 | 14.4 | 3.42 |
| DP6 | 10 | 2.84 | 6.57 | 3 | 1 | 1.8 | 6.2 |  | 4.05 |
| DP7 | 5 |  | 5.23 | 3 | 8 | 10.4 |  |  | 3.98 |
| DP8 | 5 | 2.86 | 3.71 | 23 |  |  |  |  | 4.28 |
| DP9 | 5 | 3.08 | 2.72 |  |  |  |  |  | 2.85 |
| DP10 | 5 | 0.4 | 1.99 |  |  |  |  |  | 2.08 |
| DP11 | 5 | 0.49 | 1.62 |  |  |  |  |  | 5.51 |
| DP12 | 5 | 0.8 | 1.39 |  |  |  |  |  | 0 |
| DP13 | 5 | 5.28 | 1.01 |  |  |  |  |  |  |
| DP14 | 5 |  | 14.04 |  |  |  |  |  |  |
| DP15+ | 5 |  |  |  |  |  |  |  |  |
| DP1 + 2 |  | 22.78 | 34.85 | 9 | 9 | 17.1 | 20.8 | 10.5 | 18.03 |
| DP3 + 4 |  | 59.84 | 19.93 | 59 | 82 | 50.0 | 50.1 | 75.1 | 55.68 |
| DP3/DP5 |  | 12.57 | 1.75 | 3 | n/a | 0.67 | 0.69 | n/a | 4.10 |
| DP2/DP5 |  | 9.01 | 2.48 | 2.33 | n/a | 0.63 | 0.73 | n/a | 4.12 |
| (DP3 + 4)/DP5 |  | 37.17 | 2.86 | 19.67 | n/a | 2.42 | 2.19 | n/a | 16.28 |

[1]DP1 through DP15+ given as percentages in the composition on a dry weight basis
[2]Fuji Oligo syrups are products of Nihon Shokuhin Kako Kogyo Kabushiki Kasha of Japan (Tokyo, Japan)

Example 11D—More Examples of Syrup-8A

Following the process of making Syrup-8A, more syrup batches were produced at either 50 gallon pilot production scale or 5000 gallon plant production scale. Detailed carbohydrate composition, viscosity and calculated sweetness characteristics are shown in Table 8C and 8D below.

TABLE 8C

Detailed carbohydrate composition of syrups produced at pilot and plant scales

| Lot # | Scale | DP1 | DP2 | DP3 | DP4 | DP5 | DP6 | DP7 | DP8 | DP9 | DP10 | DP11 | DP12 | DP13 | DP14 | DP15+ |
|---|---|---|---|---|---|---|---|---|---|---|---|---|---|---|---|---|
| RDCS070809A | pilot | 7.3 | 14.4 | 21.7 | 36.2 | 1.8 | 3.1 | 3.0 | 2.7 | 0.6 | 0.5 | 0.5 |  |  | 0.4 | 7.8 |
| RDCS073009 | production | 6.9 | 15.9 | 20.5 | 37.4 | 2.5 | 3.5 | 3.5 | 3.6 | 1.0 | 0.9 | 0.7 | 0.9 |  | 0.5 | 2.2 |
| RDCSP120309A |  | 6.6 | 15.5 | 19.2 | 38.9 | 2.6 | 3.5 | 3.3 | 3.8 | 1.1 | 1.0 | 0.9 | 1.8 |  |  | 1.8 |
| RDCSP120309B |  | 6.8 | 16.4 | 19.5 | 38.5 | 2.6 | 3.6 | 3.2 | 3.6 | 1.0 | 0.9 | 0.8 | 1.7 |  |  | 1.5 |
| RDCSP020310 |  | 6.1 | 13.9 | 16.2 | 42.6 | 2.4 | 3.6 | 3.3 | 4.0 | 1.2 | 1.2 | 1.0 | 1.3 | 0.9 |  | 2.2 |
| RDCSP020410 |  | 5.7 | 12.7 | 15.9 | 43.6 | 2.3 | 3.4 | 3.5 | 4.2 | 1.3 | 1.2 | 1.0 | 1.4 | 1.1 |  | 2.7 |
| RDCSP022210 |  | 5.8 | 15.5 | 19.3 | 38.5 | 2.6 | 3.6 | 3.5 | 3.7 | 1.3 | 1.1 | 1.0 | 1.3 | 0.9 |  | 2.0 |
| RDCSP050510 |  | 7.2 | 16.1 | 19.4 | 37.7 | 2.6 | 3.6 | 3.4 | 3.7 | 1.1 | 1.0 | 0.8 | 1.1 | 0.6 |  | 1.9 |
| RDCSP121510 |  | 6.2 | 16.8 | 19.8 | 37.6 | 2.8 | 3.8 | 3.5 | 3.7 | 1.2 | 1.1 | 0.8 | 2.6 |  |  | 1.9 |
| RDCSP032411 |  | 7.3 | 17.1 | 20.8 | 35.6 | 0.9 | 2.0 | 3.7 | 3.2 | 3.5 | 1.2 | 1.0 | 0.9 | 1.9 |  | 0.9 |
| RDCSP040611 |  | 6.3 | 15.8 | 20.1 | 39.0 | 2.4 | 3.3 | 3.3 | 3.7 | 1.1 | 1.0 | 0.9 | 0.7 | 1.3 |  | 1.4 |
| RDCSP042711 |  | 5.7 | 15.0 | 18.5 | 41.0 | 0.7 | 2.2 | 2.9 | 3.2 | 3.8 | 1.3 | 1.0 | 0.8 | 1.2 | 1.2 | 1.5 |
| RDCSP050411 |  | 5.6 | 15.3 | 19.7 | 39.8 | 0.6 | 2.2 | 2.9 | 3.2 | 3.7 | 1.3 | 1.0 | 0.8 | 0.7 | 1.4 | 1.8 |
| RDCSP062911 |  | 6.5 | 16.3 | 19.4 | 40.0 | 2.6 | 3.5 | 3.3 | 3.7 | 1.0 | 0.9 | 0.7 | 1.7 |  |  | 0.5 |
| 110410#8 |  | 6.1 | 15.4 | 15.4 | 48.2 | 2.1 | 3.7 | 2.8 | 3.6 | 0.6 | 0.7 | 0.5 | 0.5 | 0.5 |  |  |
| 110410#14 |  | 5.1 | 11.4 | 12.0 | 44.8 | 2.7 | 3.3 | 3.6 | 4.0 | 2.9 | 2.5 | 1.9 | 1.1 | 1.3 |  | 3.6 |
| 110410#23 |  | 7.5 | 16.3 | 16.0 | 49.7 | 1.7 | 3.2 | 1.8 | 2.3 | 0.3 | 0.4 | 0.2 | 0.6 |  |  |  |
| 111711 |  | 6.7 | 16.6 | 23.0 | 36.3 | 2.8 | 3.7 | 3.0 | 2.5 | 0.6 | 0.4 | 0.8 | 0.2 |  |  | 3.5 |
| 112211 |  | 6.7 | 16.2 | 22.2 | 34.4 | 2.2 | 3.2 | 3.1 | 2.8 | 0.9 | 0.6 | 0.5 | 0.7 |  |  | 6.6 |
| H022670 | plant production | 5.9 | 17.3 | 19.0 | 38.1 | 1.3 | 1.7 | 4.7 | 3.3 | 3.4 | 0.9 | 0.9 | 0.7 | 1.4 |  | 1.7 |
| Maximum |  | 7.5 | 17.1 | 23.0 | 49.7 | 2.8 | 3.8 | 3.7 | 4.2 | 3.8 | 2.5 | 1.9 | 2.6 | 1.9 | 1.4 | 7.8 |
| Minimum |  | 5.1 | 11.4 | 12.0 | 34.4 | 0.6 | 1.7 | 1.8 | 2.3 | 0.3 | 0.4 | 0.2 | 0.2 | 0.5 | 0.4 | 0.5 |

TABLE 8D

Detailed carbohydrate composition, viscosity and sweetness of syrups produced at pilot and plant scales.

| Lot # | Production Scale | Viscosity[1] | Calculated sweetness | Dp1 + 2 | DP3 + 4 | DP3/5 | DP2/DP5 | (DP3 + 4)/DP5 |
|---|---|---|---|---|---|---|---|---|
| RDCS070809A | pilot | 7,980 | 27 | 21.69 | 57.89 | 11.90 | 7.92 | 31.81 |
| RDCS073009 | production | 6,640 | 27 | 22.83 | 57.94 | 8.13 | 6.32 | 22.99 |
| RDCSP120309A | | 6,520 | 27 | 22.1 | 58.12 | 7.42 | 5.98 | 22.44 |
| RDCSP120309B | | 5,830 | 27 | 23.15 | 57.99 | 7.50 | 6.31 | 22.30 |
| RDCSP020310 | | 8,810 | 25 | 20.05 | 58.83 | 6.76 | 5.80 | 24.51 |
| RDCSP020410 | | 8,730 | 25 | 18.33 | 59.49 | 7.01 | 5.58 | 26.21 |
| RDCSP022210 | | 8,660 | 26 | 21.29 | 57.78 | 7.50 | 6.01 | 22.48 |
| RDCSP050510 | | 7,540 | 27 | 23.24 | 57.09 | 7.39 | 6.10 | 21.71 |
| RDCSP121510 | | 8,210 | 27 | 23.04 | 57.48 | 7.04 | 5.96 | 20.38 |
| RDCSP032411 | | 7,400 | 27 | 24.4 | 56.40 | 23.16 | 18.98 | 62.67 |
| RDCSP040611 | | 7,640 | 27 | 22.03 | 59.01 | 8.46 | 6.65 | 24.90 |
| RDCSP042711 | | 7,790 | 26 | 20.67 | 59.49 | 26.10 | 21.06 | 83.79 |
| RDCSP050411 | | 7,630 | 26 | 20.94 | 59.49 | 30.73 | 23.92 | 92.95 |
| RDCSP062911 | | 7,160 | 27 | 22.78 | 59.33 | 7.57 | 6.36 | 23.18 |
| 110410#8 | | 7,240 | 27 | 21.5 | 63.61 | 7.29 | 7.29 | 30.15 |
| 110410#14 | | 8,950 | 23 | 16.44 | 56.75 | 4.47 | 4.24 | 21.18 |
| 110410#23 | | 4,550 | 28 | 23.8 | 65.68 | 9.24 | 9.43 | 37.97 |
| 111711 | | 6,950 | 28 | 23.29 | 59.29 | 8.24 | 5.94 | 21.25 |
| 112211 | | 8,920 | 27 | 22.84 | 56.60 | 9.91 | 7.22 | 25.27 |
| H022670 | plant production | 6,500 | 26 | 23.16 | 57.00 | 14.92 | 13.60 | 44.88 |
| maximum | | 8950 | 28 | 24.4 | 65.68 | 30.73 | 23.92 | 92.95 |
| minimum | | 4550 | 23 | 16.44 | 56.4 | 4.47 | 4.24 | 20.38 |

[1]Viscosity (cPs) measured at 78% DS and 100° F.

Example 11E—Moisture Uptake and Retention of Syrup RDCSP020410 (Table 8C) and Syrup A (Table 7)

Detailed carbohydrate compositions of Syrup RDCSP020410 (Syrup '410) in Table 8C and Syrup A in Table 7 and conventional corn syrups of 28DE, 36DE and 43DE (commercially available from Cargill, Incorporated, Wayzata, Minn.) are shown in Table 8E.

TABLE 8E

Detailed carbohydrate compositions as compared to conventional corn syrups

| Composition (% dry weight basis) | Carbohydrate compositions | | Traditional corn syrup carbohydrates | | |
|---|---|---|---|---|---|
| | Syrup '410[1] (Table 8C) | Syrup A (Table 7) | 28DE CS | 36DE CS | 43DE CS |
| DP1 | 5.7 | 3.3 | 6.4 | 16.1 | 17.6 |
| DP2 | 12.7 | 19.2 | 6.8 | 10.5 | 17.3 |
| DP3 | 15.9 | 48.7 | 8.5 | 12.4 | 12.2 |
| DP4 | 43.6 | 8.2 | 7.0 | 10.4 | 7.8 |
| DP5 | 2.3 | 3.1 | 6.6 | 8.2 | 7.0 |
| DP6 | 3.4 | 5.5 | 8.7 | 8.2 | 6.6 |
| DP7 | 3.5 | 1.8 | 8.3 | 6.4 | 5.2 |
| DP8 | 4.2 | 0.8 | 4.9 | 3.2 | 3.7 |
| DP9 | 1.3 | 0.8 | 3.5 | 2.3 | 2.7 |
| DP10 | 1.2 | 0.4 | 2.2 | 2.1 | 2.0 |
| DP11+ | 6.2 | 8.2 | 37.1 | 20.2 | 17.9 |
| DP1 + DP2 | 18.4 | 22.5 | 13.2 | 26.6 | 34.9 |
| DP3 + DP4 | 59.5 | 56.9 | 15.5 | 22.8 | 20.0 |
| DP2/DP5 | 5.52 | 6.19 | 1.03 | 1.28 | 2.47 |
| DP3/DP5 | 6.91 | 15.71 | 1.28 | 1.51 | 1.74 |

[1]A portion of '410 syrup was passed through a cation exchange column packed with Dowex 88 resin followed by passing through an anion exchange column packed with Dowex 66 resin before concentrated in a rotary evaporator to about 80% DS (i.e., a de-ashed '410 syrup). The de-ashed '410 syrup had the same carbohydrate composition as the '410 syrup without de-ash treatment).

Figure 5:
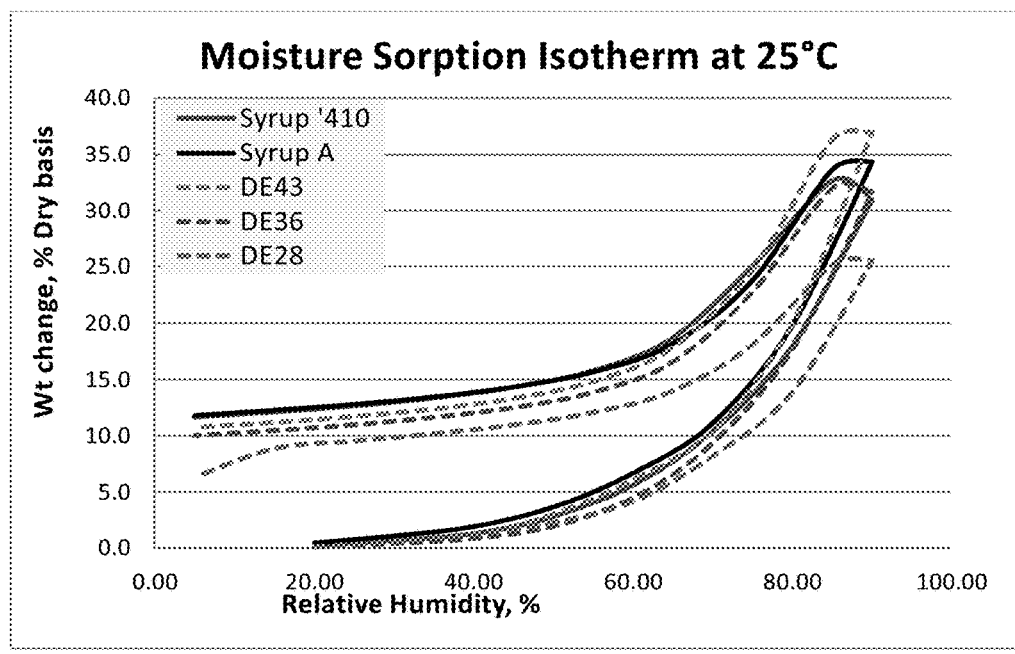
FIG. 5 is a graph of moisture sorption isotherm data of certain syrup samples of the present invention and conventional starch-derived corn syrup products.

Moisture sorption isotherm tests of Syrup '410 in Table 8C and Syrup A in Table 7 were conducted at 25° C. and relative humidity of 20-90% (adsorption) and 90-5% (desorption) and compared to the adsorption and desorption properties of conventional 28DE, 36DE and 43DE corn syrups. As shown in FIG. 5, with respect to conventional syrups, as total mono- and di-saccharides increased, which corresponds to an increase in DE, moisture uptake increased during adsorption with an increase in relative humidity. For example, a 43 DE syrup had higher moisture uptake compared to a 36 DE syrup and a 28 DE syrup, and a 36 DE syrup had a higher moisture uptake compared to a 28 DE syrup. During desorption with decreasing relative humidity, as total mono- and di-saccharides increased, which corresponds to an increase in DE, moisture retention increased. In comparison, surprisingly, the carbohydrate compositions of Syrup '410 (de-ashed) and Syrup A, each containing only about 18% and 23% total mono- and di-saccharides respectively (see Table 8E), showed adsorption similar to a 36 DE syrup (about 27% total mono- and di-saccharides) and/or a 43DE syrup (about 35% total mono- and di-saccharides). More surprisingly, the carbohydrate compositions of Syrup '410 (de-ashed) and Syrup A showed higher moisture retention during desorption when subjected to decreasing relative humidity from about 90% to about 5% than a 43 DE syrup that contained 48% and 36% more total mono- and di-saccharides than current carbohydrate composition Syrup '410 of Table 8C and Syrup A of Table 7 respectively. It is believed that the surprising adsorption and desorption isotherm results are attributable to the unique carbohydrate profile (e.g., low total mono- and di-saccharide, low DP11+ polymers, high DP3+DP4, and high DP2/DP5 and DP3/DP5 ratios) of the carbohydrate compositions.

The results of the adsorption-desorption isotherm test indicate that the carbohydrate compositions of the present invention are useful to prepare a broad range of food products where increasing humectancy, without increasing hygroscopicity, is needed.

Example 12—Chromatographic Separation of Mono- and Disaccharides from Low-Viscosity Reduced-Sugar Syrup The low-viscosity reduced-sugar syrup of Example 9-E at about 60% DS was loaded to a column packed with Mitsubishi UBK-550 resin in sodium form for a chromatographic column separation of DP1 and DP2 using water as an eluent. As shown in Table 9, a series of products with DP1+DP2 as low as 0% could be obtained with relatively high yields. This example shows that by removing DP1 and DP2 from the low-viscosity sugar-reduced syrup, a sugar-free product can be obtained.

TABLE 9

DP profile of syrup products of Example 12

| yield (%) | DP3+ | DP1 + DP2 |
|---|---|---|
| 100 | 88.56 | 11.44 |
| 99 | 88.62 | 11.38 |
| 96 | 88.80 | 11.20 |
| 92 | 89.92 | 10.08 |
| 90 | 90.52 | 9.48 |
| 86 | 91.72 | 8.28 |
| 80 | 94.01 | 5.99 |
| 73 | 96.92 | 3.08 |
| 63 | 99.05 | 0.95 |
| 51 | 99.87 | 0.13 |
| 33 | 100.00 | 0.00 |
| 14 | 100.00 | 0.00 |
| 2 | 100.00 | 0.00 |

Example 13—Syrup Made Under Various Temperature Conditions

An enzyme-liquefied starch slurry of about 12 DE, 36.9% DS, and pH of about 6.1 was obtained from a Cargill corn milling plant. The liquefied liquor was then cooled to about 145° F., adjusted to a pH of about 4.5 with HCl solution, and about 0.1% of a pullulanase (Optimax L-1000, Genencor International, Rochester, N.Y.), measured on a dry weight basis of starch, was added for saccharification at about 86° F., about 104° F., about 122° F., about 140° F., about 149° F., about 158° F. and about 176° F. for about 10 to about 70 hours with mild agitation. The carbohydrate profile of the syrup products are shown in Table 10. While products obtained at from about 120° F. to about 160° F. are preferred, it is understood by one skilled in the arts of syrup making that the reaction at the lower temperature will take longer time to complete.

TABLE 10

DP profile of syrup products of Example 13.

| | Temperature | | | | | | |
|---|---|---|---|---|---|---|---|
| | 86° F. | 104° F. | 122° F. | 140° F. | 149° F. | 158° F. | 176° F. |
| DP1 | 1.0 | 1.2 | 2.1 | 2.7 | 3.2 | 3.8 | 4.6 |
| DP2 | 8.0 | 10.5 | 12.8 | 13.0 | 13.7 | 14.0 | 13.6 |
| DP3 | 15.5 | 18.7 | 20.9 | 17.9 | 17.9 | 17.8 | 14.4 |
| DP4 | 7.2 | 8.4 | 9.0 | 8.2 | 8.2 | 8.2 | 0.0 |
| DP5 | 11.4 | 14.5 | 17.2 | 22.6 | 23.4 | 24.0 | 24.9 |
| DP6 | 14.6 | 15.1 | 18.5 | 18.9 | 19.1 | 17.0 | 16.0 |
| DP7 | 8.6 | 4.4 | 0.0 | 1.7 | 2.1 | 0.0 | 0.9 |
| DP8 | 0.0 | 0.9 | 2.5 | 0.0 | 0.0 | 0.0 | 0.0 |
| DP9 | 0.0 | 1.0 | 1.9 | 3.6 | 3.2 | 5.6 | 3.5 |
| DP10 | 1.6 | 1.8 | 0.6 | 1.7 | 1.7 | 1.9 | 2.3 |
| DP11 | 0.0 | 0.0 | 0.5 | 3.2 | 3.2 | 3.0 | 0.0 |
| DP12 | 0.0 | 0.0 | 1.0 | 0.0 | 0.0 | 0.0 | 0.0 |
| DP13 | 0.0 | 0.0 | 0.0 | 0.0 | 0.0 | 0.0 | 0.0 |
| DP14 | 0.0 | 0.0 | 0.0 | 0.0 | 0.0 | 0.0 | 0.0 |
| DP15+ | 32.3 | 23.5 | 13.2 | 6.5 | 4.3 | 4.8 | 19.9 |
| DP1 + 2 | 8.9 | 11.7 | 14.9 | 15.7 | 16.9 | 17.8 | 18.2 |
| DP3-7 | 57.2 | 61.2 | 65.5 | 69.3 | 70.7 | 66.9 | 56.2 |
| DP3-10 | 58.8 | 64.8 | 70.5 | 74.6 | 75.7 | 74.4 | 61.9 |
| DP3-14 | 58.8 | 64.8 | 72.0 | 77.8 | 78.8 | 77.4 | 61.9 |
| Oligosaccharide Index-I | 1.8 | 2.8 | 4.8 | 7.7 | 10.1 | 9.6 | 3.1 |
| Oligosaccharide index-II | 1.8 | 2.8 | 5.5 | 11.9 | 18.4 | 16.3 | 3.1 |
| DE | 22 | 25 | 29 | 30 | 31 | 31 | 28 |

Example 14—Syrup Made Under Various pH Conditions

An enzyme-liquefied starch slurry of about 12 DE, about 36.9% dry solids (DS), and pH of about 6.1 was obtained from a Cargill corn milling plant. The liquefied liquor was then cooled to about 145° F., adjusted to a pH of about 3.0, about 4.0, about 4.5, and about 5.0 with HCl solution, unchanged, and a pH of about 7.0 with NaOH solution, and about 0.1% of a pullulanase (Optimax L-1000, Genencor International, Rochester, N.Y.), measured on a dry weight basis of starch, was added for saccharification at about 150° F. for about 10 to about 70 hours with mild agitation. The carbohydrate profile of the syrup products are shown in Table 11. The example demonstrates that low-viscosity reduced-sugar syrup varieties can be obtained at various pH conditions, although a pH of about 4.5 to about 6.0 is preferred.

TABLE 11

DP Profile of syrup made under various pH conditions

| pH | 3 | 4 | 4.5 | 5 | 6.0 | 7.0 |
|---|---|---|---|---|---|---|
| DP1 | 0.9 | 1.4 | 3.2 | 3.6 | 3.2 | 2.9 |
| DP2 | 5.1 | 8.4 | 13.7 | 13.8 | 13.4 | 12.5 |
| DP3 | 9.7 | 14.0 | 17.9 | 17.9 | 18.8 | 17.0 |
| DP4 | 5.3 | 6.8 | 8.2 | 8.3 | 8.0 | 7.1 |
| DP5 | 6.2 | 10.7 | 23.4 | 23.0 | 20.3 | 20.3 |
| DP6 | 13.4 | 20.5 | 19.1 | 18.7 | 13.3 | 13.9 |
| DP7 | 13.2 | 10.7 | 2.1 | 1.9 | 0.0 | 0.0 |
| DP8 | 0.0 | 0.0 | 0.0 | 3.6 | 2.1 | 1.9 |
| DP9 | 2.2 | 0.0 | 3.2 | 0.5 | 3.0 | 2.5 |
| DP10 | 0.0 | 2.2 | 1.7 | 1.1 | 2.3 | 2.3 |
| DP11 | 0.0 | 0.8 | 3.2 | 3.3 | 1.7 | 1.4 |
| DP12 | 0.0 | 0.0 | 0.0 | 0.0 | 1.6 | 0.0 |
| DP13 | 0.0 | 0.0 | 0.0 | 0.0 | 0.0 | 0.0 |
| DP14 | 0.0 | 0.0 | 0.0 | 0.0 | 0.0 | 0.0 |
| DP15+ | 44.1 | 24.7 | 4.3 | 4.4 | 12.5 | 18.1 |
| DP1 + 2 | 6.0 | 9.7 | 16.9 | 17.3 | 16.5 | 15.5 |
| DP3-7 | 47.7 | 62.6 | 70.7 | 69.8 | 60.3 | 58.3 |
| DP3-10 | 49.9 | 64.8 | 75.7 | 75.0 | 67.7 | 65.0 |
| DP3-14 | 49.9 | 65.6 | 78.8 | 78.3 | 71.0 | 66.4 |
| Oligosaccharide Index-I | 1.1 | 2.5 | 10.1 | 9.8 | 4.3 | 3.3 |
| Oligosaccharide index-II | 1.1 | 2.7 | 18.4 | 18.0 | 5.7 | 3.7 |
| DE | 18 | 23 | 31 | 31 | 29 | 28 |

Example 15—Syrup Made Under Various Solids Levels

An acid-liquefied starch slurry (about 20 DE, 46.9% DS, pH of about 4.9) was obtained from a Cargill corn milling plant. The liquefied liquor was cooled to about 145° F. and adjusted to dry solids level of about 10%, about 20%, about 30%, about 40%, about 50%, about 60% and about 70% DS. To the temperature- and solids-adjusted starch liquor, about 0.005% of an alpha-amylase (BAN 480, Novo Nordisk, Denmark) and about 0.1% of a pullulanase (Optimax L-1000, Genencor International, Rochester, N.Y.), measured on a dry weight basis of starch, were added for saccharification at about 150° F. for about 17 hours to about 66 hours with mild agitation. The carbohydrate profile of the final syrup product is shown in Table 12. This example shows that low-viscosity reduced-sugar syrups can be obtained by varying substrate concentrations, although substrate concentrations of about 30 to about 60% DS are preferred. It is also understood by one skilled in the art that a longer period of time is needed for the reaction to complete at higher DS levels.

TABLE 12

DP profile of syrup products of Example 15.

| % DS | 10 | 20 | 30 | 40 | 50 | 60 | 70 |
|---|---|---|---|---|---|---|---|
| DP1 | 5 | 5 | 5 | 6 | 6 | 6 | 5 |
| DP2 | 6 | 6 | 7 | 11 | 11 | 10 | 9 |
| DP3 | 7 | 7 | 10 | 13 | 13 | 13 | 11 |
| DP4 | 7 | 7 | 9 | 10 | 10 | 9 | 8 |
| DP5 | 8 | 7 | 9 | 12 | 12 | 11 | 9 |
| DP6 | 9 | 8 | 14 | 19 | 18 | 15 | 11 |
| DP7 | 7 | 7 | 11 | 8 | 7 | 6 | 6 |
| DP8 | 6 | 6 | 5 | 0 | 0 | 0 | 0 |
| DP9 | 0 | 0 | 5 | 4 | 4 | 0 | 0 |
| DP10 | 6 | 6 | 0 | 4 | 4 | 8 | 6 |
| DP11 | 0 | 0 | 0 | 3 | 3 | 3 | 0 |
| DP12 | 0 | 0 | 0 | 6 | 6 | 2 | 0 |
| DP13 | 0 | 0 | 0 | 0 | 0 | 0 | 0 |
| DP14 | 0 | 0 | 0 | 0 | 0 | 0 | 0 |
| DP15+ | 39 | 40 | 25 | 5 | 6 | 16 | 33 |
| DP1 + 2 | 11 | 10 | 12 | 17 | 17 | 16 | 14 |
| DP3-7 | 39 | 38 | 53 | 62 | 60 | 55 | 47 |
| DP3-10 | 51 | 50 | 63 | 69 | 67 | 63 | 53 |
| DP3-14 | 51 | 50 | 63 | 79 | 77 | 68 | 53 |
| Oligosaccharide Index-I | 1.3 | 1.2 | 2.5 | 5.0 | 4.4 | 3.0 | 1.6 |
| Oligosaccharide index-II | 1.3 | 1.2 | 2.5 | 16.0 | 12.6 | 4.2 | 1.6 |
| DE | 21 | 21 | 24 | 29 | 30 | 28 | 25 |

Example 16—Substrates with Varying DE are Used for Making Low-Viscosity Reduced-Sugar Syrup Dry powder maltodextrin products, commercially available from Cargill, Incorporated (Wayzata, Minn.), were made to about 30% DS syrup with 0.02 N lactic acid buffer at a pH of about 4.7 to about 4.8. Conventional corn syrup products, commercially available from Cargill, Incorporated (Wayzata, Minn.) were diluted to about 30% DS with 0.02 N lactic acid buffer at a pH of about 4.8 to about 4.9. All samples were equilibrated at about 150° F. and about 0.2% of an enzyme mix consisting of an alpha-amylase (BAN 480, Novo Nordisk, Denmark) and a pullulanase (Optimax L-1000, Genencor International, Rochester, N.Y.), measured on a dry weight basis of starch, were added for saccharification at about 145° F. to about 150° F. for about 7 hours. DP composition of the starting raw material maltodextrins and corn syrups is shown in Table 13 while that of resulting syrups in Table 14. This example demonstrates that low-viscosity reduced-sugar syrup can also be made using starch hydrolysates such as maltodextrins and conventional syrups with varying DEs, although substrates with DE of less than about 25 are preferred.

TABLE 13

DP profile of the starting substrates with varying DE used for making low-viscosity reduced sugar syrup

| Profile | Maltodextrin/corn syrup solids | | | | | | Corn syrup | | | | |
|---|---|---|---|---|---|---|---|---|---|---|---|
| | 5DE | 10DE | 13DE | 18DE | 21DE | 25DE | 25DE | 28DE | 36DE | 43DE | 63DE |
| DP15+ | 85.9 | 58.9 | 47.3 | 49.6 | 45.1 | 29.8 | 36.4 | 29.2 | 24.0 | 14.0 | 2.5 |
| DP14 | 0.0 | 0.0 | 0.0 | 0.0 | 0.0 | 0.0 | 0.0 | 0.0 | 0.0 | 0.0 | 0.0 |
| DP13 | 0.0 | 0.0 | 0.0 | 0.0 | 0.0 | 0.0 | 0.0 | 0.0 | 0.0 | 0.0 | 0.9 |
| DP12 | 0.0 | 0.0 | 0.0 | 0.0 | 0.0 | 0.0 | 0.0 | 0.0 | 0.0 | 0.0 | 0.6 |
| DP11 | 0.0 | 0.0 | 0.0 | 0.0 | 0.0 | 1.5 | 0.0 | 0.0 | 0.0 | 2.0 | 0.9 |
| DP10 | 0.0 | 2.5 | 1.6 | 0.0 | 2.3 | 1.6 | 0.0 | 0.0 | 0.0 | 0.0 | 1.1 |
| DP9 | 2.2 | 3.3 | 2.5 | 1.9 | 1.5 | 1.7 | 3.5 | 3.2 | 4.2 | 2.4 | 1.2 |
| DP8 | 2.2 | 4.4 | 4.0 | 2.8 | 1.6 | 0.0 | 4.8 | 4.3 | 4.4 | 2.8 | 1.7 |
| DP7 | 2.6 | 7.6 | 9.5 | 6.8 | 4.3 | 4.7 | 8.2 | 9.2 | 6.9 | 5.8 | 2.3 |
| DP6 | 2.2 | 8.4 | 13.1 | 12.7 | 13.3 | 19.4 | 9.8 | 11.8 | 8.6 | 8.8 | 3.1 |
| DP5 | 1.2 | 3.2 | 4.9 | 6.9 | 9.3 | 11.0 | 6.9 | 7.7 | 7.8 | 8.0 | 4.1 |
| DP4 | 1.3 | 2.8 | 3.9 | 4.0 | 4.3 | 6.3 | 7.1 | 7.6 | 8.7 | 8.3 | 4.9 |
| DP3 | 1.3 | 5.7 | 8.3 | 8.0 | 8.5 | 11.7 | 8.9 | 10.1 | 10.7 | 12.3 | 8.8 |
| DP2 | 0.8 | 2.8 | 4.5 | 5.7 | 7.5 | 9.9 | 8.4 | 9.6 | 12.3 | 15.0 | 29.3 |
| Dextrose | 0.3 | 0.5 | 0.6 | 1.6 | 2.4 | 2.5 | 6.0 | 7.1 | 12.2 | 20.4 | 38.2 |
| DP1 + 2 | 1.1 | 3.3 | 5.0 | 7.3 | 9.9 | 12.4 | 14.4 | 16.8 | 24.5 | 35.4 | 67.5 |
| DP3-7 | 8.6 | 27.7 | 39.7 | 38.4 | 39.6 | 53.1 | 40.9 | 46.5 | 42.7 | 43.3 | 23.1 |
| DP15+ | 85.9 | 58.9 | 47.3 | 49.6 | 45.1 | 29.8 | 36.4 | 29.2 | 24.0 | 14.0 | 2.5 |

TABLE 14

DP profile of syrup products made from maltodextrins and corn syrups with varying DE

| | Feedstock | | | | | | | | | | |
|---|---|---|---|---|---|---|---|---|---|---|---|
| | Maltodextrin/corn syrup solids | | | | | | Corn syrup | | | | |
| DE | 5DE | 10DE | 13DE | 18DE | 21DE | 25DE | 25DE | 28DE | 36DE | 43DE | 63DE |
| | DP profile of resulting syrup products | | | | | | | | | | |
| DP1 | 1.8 | 4.2 | 3.4 | 4.3 | 4.5 | 5.0 | 8.2 | 10.3 | 14.4 | 21.5 | 38.2 |
| DP2 | 9.0 | 14.3 | 13.0 | 13.5 | 13.9 | 15.4 | 15.3 | 16.5 | 17.4 | 18.0 | 29.7 |
| DP3 | 13.7 | 17.0 | 16.3 | 16.2 | 16.1 | 17.4 | 15.7 | 16.7 | 15.9 | 15.5 | 10.6 |
| DP4 | 9.3 | 9.7 | 9.1 | 9.3 | 9.3 | 10.2 | 10.7 | 10.8 | 11.2 | 10.3 | 7.0 |
| DP5 | 10.2 | 15.5 | 14.1 | 15.1 | 16.5 | 17.5 | 14.9 | 15.5 | 13.8 | 11.9 | 5.3 |
| DP6 | 23.6 | 22.0 | 24.1 | 22.7 | 21.9 | 21.7 | 18.4 | 14.9 | 12.8 | 10.0 | 3.4 |
| DP7 | 11.2 | 3.4 | 4.5 | 4.2 | 3.5 | 3.2 | 4.0 | 3.9 | 4.2 | 4.0 | 2.1 |
| DP8 | 2.6 | 2.1 | 2.2 | 2.6 | 3.0 | 2.2 | 3.7 | 3.6 | 3.4 | 2.9 | 3.3 |
| DP9 | 2.3 | 1.8 | 1.8 | 1.9 | 1.7 | 1.1 | 2.5 | 2.5 | 7.0 | 5.6 | |
| DP10 | 1.4 | 1.3 | 1.0 | 1.2 | 1.2 | 2.1 | 6.6 | 5.5 | 0.0 | 0.0 | 0.0 |
| DP11 | 1.4 | 2.0 | 2.6 | 2.5 | 2.2 | 0.0 | 0.0 | 0.0 | 0.0 | 0.0 | 0.0 |
| DP12 | 1.4 | 0.0 | 0.0 | 0.0 | 0.0 | 0.0 | 0.0 | 0.0 | 0.0 | 0.0 | 0.0 |
| DP13 | 1.3 | 0.0 | 0.0 | 0.0 | 0.0 | 0.0 | 0.0 | 0.0 | 0.0 | 0.0 | 0.0 |
| DP14 | 0.0 | 0.0 | 0.0 | 0.0 | 0.0 | 0.0 | 0.0 | 0.0 | 0.0 | 0.0 | 0.0 |
| DP15+ | 10.8 | 6.9 | 7.9 | 6.9 | 6.1 | 4.4 | 0.0 | 0.0 | 0.0 | 0.0 | 0.0 |
| DP1 + 2 | 10.8 | 18.4 | 16.4 | 17.7 | 18.4 | 20.4 | 23.6 | 26.7 | 31.7 | 39.5 | 67.9 |
| DP3-7 | 67.9 | 67.6 | 68.1 | 67.4 | 67.3 | 70.0 | 63.7 | 61.7 | 57.9 | 51.6 | 28.3 |
| DP3-10 | 74.3 | 72.6 | 73.1 | 73.0 | 73.3 | 75.3 | 76.4 | 73.3 | 68.3 | 60.2 | 31.6 |
| DP3-14 | 78.4 | 74.7 | 75.7 | 75.4 | 75.5 | 75.3 | 76.4 | 73.3 | 68.3 | 60.2 | 31.6 |
| Oligosaccharide Index-I | 5.0 | 8.1 | 7.0 | 7.8 | 8.8 | 17.3 | >100 | >100 | >100 | 188.1 | 61.9 |
| Oligosaccharide index-II | 7.2 | 10.8 | 9.5 | 11.0 | 12.3 | 17.3 | >100 | >100 | >100 | >100 | >100 |
| DE | 25 | 31 | 29 | 30 | 31 | 33 | 35 | 37 | 41 | 47 | 63 |

Example 17—Low-Viscosity and Reduced-Sugar Syrups Made from Various Starches

Native wheat, rice and potato starch (all obtained from Sigma-Aldrich, St Louis, Mo.) and native tapioca starch (obtained from Cargill, Wayzata, Minn.) were made to about 36% DS (w/w) slurry with water containing about 200 ppm lactic acid and adjusted to a pH of about 5.9 with dilute lime slurry. After adding about 0.075% of Spezyme Fred-L (Genencor International, Rochester, N.Y.) on starch dry weight basis, the starch slurries were liquefied at about 200° F. to about 205° F. The liquefied starch solutions were cooled to about 150° F., readjusted to pH of about 4.7 with HCl solution, and reacted with about 0.05% Spezyme LT-75 (a low temperature amylase from Genencor International, Rochester, N.Y.) and about 0.15% Optimax L-1000 (a pullulanase from Genencor International, Rochester, N.Y.) at about 150° F. for about 19 hours. The resulting syrups had about 13% to about 16% total mono- and di-saccharides, about 8 to about 13% DP15+, and greater than about 60% of DP3-10, and greater than about 70% of DP3-DP14, resulting in First Oligosaccharide Index of greater than about 2.0 and Second Oligosaccharide Index of greater than about 3.0. Detailed carbohydrate compositions of the resulting syrups are shown in Table 15.

TABLE 15

DP profile of syrups made from various starches of Example 17

| Profile | Potato | Rice | Tapioca | Wheat |
|---|---|---|---|---|
| DP1 | 4.1 | 2.3 | 2.6 | 2.9 |
| DP2 | 11.6 | 10.5 | 11.0 | 12.1 |
| DP3 | 14.8 | 14.4 | 15.8 | 17.6 |
| DP4 | 8.8 | 9.3 | 10.1 | 10.6 |
| DP5 | 11.0 | 11.5 | 12.2 | 13.2 |
| DP6 | 17.9 | 22.4 | 22.5 | 19.8 |
| DP7 | 5.7 | 8.5 | 6.9 | 6.6 |
| DP8 | 4.4 | 2.2 | 1.4 | 2.8 |
| DP9 | 3.7 | 2.4 | 3.6 | 2.6 |
| DP10 | 1.4 | 1.6 | 1.7 | 1.7 |
| DP11 | 1.5 | 1.2 | 1.3 | 1.2 |
| DP12 | 1.3 | 1.0 | 1.2 | 1.2 |
| DP13 | 1.4 | 0.0 | 0.0 | 0.0 |
| DP14 | 1.3 | 0.0 | 0.0 | 0.0 |
| DP15+ | 11.2 | 12.9 | 9.8 | 7.8 |
| DP1 + 2 | 15.7 | 12.8 | 13.6 | 15.0 |
| DP3-7 | 58.2 | 66.0 | 67.6 | 67.8 |
| DP3-10 | 67.7 | 72.2 | 74.2 | 74.8 |
| DP3-14 | 73.2 | 74.4 | 76.7 | 77.2 |
| Oligosaccharide Index-I | 4.1 | 4.8 | 6.0 | 7.3 |
| Oligosaccharide index-II | 6.6 | 5.8 | 7.8 | 9.9 |
| DE | 25 | 25 | 25 | 25 |

Example 18—Low-Viscosity and Reduced-Sugar Syrup Made from Dent and Waxy Corn Starches Native dent corn starch slurry was obtained from a Cargill corn milling plant while a native waxy corn starch was purchased from Sigma-Aldrich (St. Louis, Mo., USA). Starch slurries were made to about 36% DS, adjusted to a pH of about 5.7 with dilute lime solution and liquefied with either Spezyme Fred-L (Genencor International, Rochester, N.Y.) or Fuelzyme-LF (Verenium, San Diego, Calif.), both amylases, at dosages of about 0.075% on starch dry weight basis at about 200° F. to about 205° F. The liquefied starch solutions were cooled to about 150° F., readjusted to pH of about 4.5 with $H_2SO_4$ solution and reacted with about 0.3% isoamylase (Hayashibara, Okayama, Japan) and about 0.3% pullulanase (Optimax L-1000, Genencor International, Rochester, N.Y.) at about 150° F. for about 23 hours. The resulting syrups from dent corn starch had about 11% to about 17% total mono- and di-saccharides, greater than about 60% DP3-DP10, and greater than about 70% DP3-DP14 with no DP15+. Syrups made from waxy corn starch contained about 14% to about 17% total mono- and di-saccharides, greater than about 60% DP3-DP10, and greater than about 70% DP3-DP14 with no DP15+ for the treatment with Fuelzyme-LF and only about 4% DP15+ for the treatment with Spezyme Fred-L. All syrups had First Oligosaccharide Index of greater than about 2.0 and Second Oligosaccharide Index of about 3.0. Detailed carbohydrate compositions of the resulting syrups are shown in the Table 16.

TABLE 16

Dp profile of syrups made from dent and waxy corn starches of Example 18

| | Feedstock | | | |
|---|---|---|---|---|
| | Dent Corn Starch | | Waxy Corn Starch | |
| Enzyme | Fred-L | Fuelzyme-LF | Fred-L | Fuelzyme-LF |
| DP1 | 1.7 | 3.2 | 2.5 | 3.6 |
| DP2 | 9.6 | 14.0 | 11.2 | 13.7 |
| DP3 | 18.4 | 14.3 | 20.2 | 13.8 |
| DP4 | 9.9 | 12.0 | 9.7 | 11.9 |
| DP5 | 19.1 | 10.9 | 24.2 | 10.8 |
| DP6 | 17.1 | 17.5 | 15.5 | 18.0 |
| DP7 | 7.6 | 10.7 | 4.3 | 11.1 |
| DP8 | 2.7 | 3.7 | 0.0 | 3.3 |
| DP9 | 2.6 | 3.6 | 2.5 | 3.6 |
| DP10 | 2.6 | 2.8 | 1.9 | 2.9 |
| DP11 | 2.0 | 1.9 | 1.3 | 2.0 |
| DP12 | 6.9 | 5.2 | 2.6 | 5.4 |
| DP13 | 0.0 | 0.0 | 0.0 | 0.0 |
| DP14 | 0.0 | 0.0 | 0.0 | 0.0 |
| DP15+ | 0.0 | 0.0 | 4.1 | 0.0 |
| DP1 + 2 | 11.3 | 17.2 | 13.7 | 17.3 |
| DP3-7 | 72.0 | 65.5 | 74.0 | 65.5 |
| DP3-10 | 79.8 | 75.6 | 78.4 | 75.4 |
| DP3-14 | 88.7 | 82.8 | 82.2 | 82.7 |
| Oligosaccharide Index-I | 9.0 | 10.5 | 9.9 | 10.3 |
| Oligosaccharide index-II | >100 | >100 | 20.1 | >100 |
| DE | 28 | 29 | 30 | 30 |

Example 19—Viscosity and Carbohydrate Composition of Low-Viscosity Reduced-Sugar Syrups as Compared with Conventional Starch-Derived Products Viscosities of various low-viscosity reduced-sugar syrups and that of conventional 28DE syrup were measured at about 78% DS and at about 100° F. Because of the extremely high viscosity, the viscosities of conventional 5DE and 13DE maltodextrins were measured at much lower dry solid concentrations and their minimal viscosities estimated according to D'Haene and van Leiderkerk ("Viscosity prediction of starch hydrolysates from single point measurements", Starch/Starke, 48:327-334 (1996)). As shown in Table 17, the low-viscosity reduced-sugar syrups of the present invention exhibited significantly lower viscosities, ranging from at least about 40% to more than about 99% lower, as compared to conventional products at total mono- and di-saccharides ranging from about 0% to about 25%. As readily seen, syrups of the present invention provide substantially unique carbohydrate compositions with very high levels of oligosaccharides as characterized by First Oligosaccharide Index of greater than about 2.0 and Second Oligosaccharide Index of greater than about 3.0. Compared to commercial starch derived products having similar DE, the First and Second Oligosaccharide Indices of the present invention are substantially higher.

TABLE 17

Viscosity and carbohydrate profile comparison between low-viscosity reduced-sugar syrups and those of conventional syrup and maltodextrins products at similar total mono- and disaccharide levels.

| | Carbohydrate profile | | | | | | | | |
|---|---|---|---|---|---|---|---|---|---|
| Comparative samples | DE | DP1 + 2 | DP3-10 | DP11+ | Oligosaccharide Index-I | DP3-14 | DP15+ | Oligosaccharide Index-II | Viscosity* 78% DS 100 F. |
| conventional, 5DE maltodextrin | 5 | 1 | 13 | 86 | 0.2 | 13 | 86 | 0.2 | 64,000,000* |
| current invention, Example 12 | 20 | 0.5 | 84 | 16 | 5.3 | 97 | 3 | 32.3 | 51,000 |
| current invention, Example 11B | 28 | 2 | 90 | 8 | 11.3 | 92 | 6 | 15.3 | 28,000 |
| conventional, 13DE maltodextrin | 13 | 5 | 48 | 47 | 1.0 | 48 | 47 | 1.0 | 630,000* |
| current invention, Example 10F | 32 | 8 | 88 | 4 | 22.0 | 91 | 1 | 91.0 | 9,500 |
| current invention, Example 9E | 27 | 11 | 77 | 12 | 6.4 | 83 | 6 | 13.8 | 11,000 |
| conventional, 28DE syrup | 28 | 16 | 56 | 28 | 2.0 | 56 | 28 | 2.0 | 40,000 |
| current invention, Example 4 | 29 | 17 | 63 | 20 | 3.2 | 71 | 12 | 5.9 | 12,500 |
| conventional, 36DE syrup | 36 | 27 | 53 | 20 | 2.6 | 55 | 19 | 2.9 | 20,000 |
| current invention, Example 10D | 37 | 21 | 73 | 6 | 12.2 | 77 | 2 | 38.5 | 8,200 |
| current invention, Example 11A | 38 | 23 | 71 | 6 | 11.8 | 72 | 5 | 14.4 | 7,800 |

The data presented in the above tables demonstrates that the low-viscosity reduced-sugar syrup of the present invention is novel and contains a very unique carbohydrate profile. Specifically, the low-viscosity reduced-sugar syrup described herein has low levels of simple sugars (DP1, DP2), is greatly enriched in oligosaccharides (DP3-10 and DP3-14 in particular), characterized by First Oligosaccharide Index of greater than about 2.0 and Second Oligosaccharide Index of greater than about 3.0, and has very low level of less than about 15% of DP15+. The low-viscosity reduced-sugar syrup of the present invention has a DE of about 20 to about 52 with significantly less viscosities than conventional starch-derived products having a similar total mono- and di-saccharides or a similar DE. In addition, the low-viscosity reduced-sugar syrup described herein is clear in appearance and is free of any haze.

Figure 2:
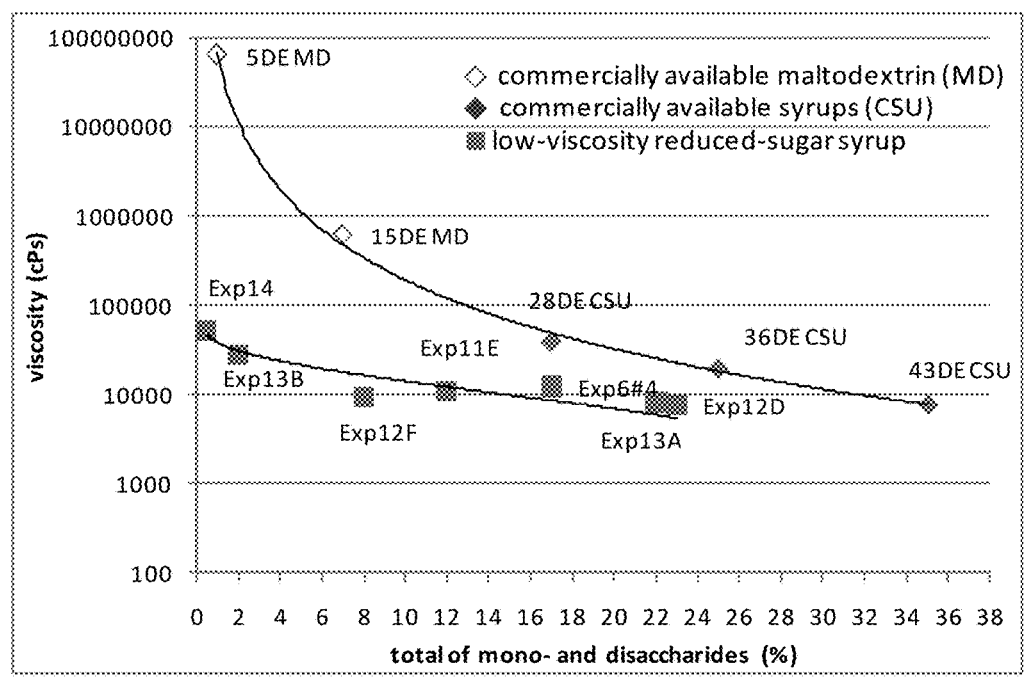
FIG. 2 is a graph of the data of certain syrup samples of the present invention and conventional starch-derived products in Examples 4, 9, 10, 11, and 12.

Referring to the Figures, FIG. 2 illustrates low-viscosity reduced-sugar syrups having less than about 25% total mono- and di-saccharides have significantly lower viscosities as compared to conventional syrup and maltodextrin products at similar levels of total mono- and di-saccharides. For example, a low-viscosity reduced-sugar syrup is significantly lower than a conventional syrup of DE of about 28. Viscosities of the syrups of the present invention and conventional syrups were measured at about 78% dry solids and about 100° F. The viscosities of the maltodextrins at a DE of 5 and 15 were estimated according to D'Haene and van Leiderkerk ("Viscosity prediction of starch hydrolysates from single point measurements", *Starch/Starke*, 48:327-334 (1996)) because it was not possible to accurately measure the viscosities of 5 DE and 15 DE maltodextrins at about 78% dry solids and about 100° F. due to their extremely high viscosities.

Figure 3:
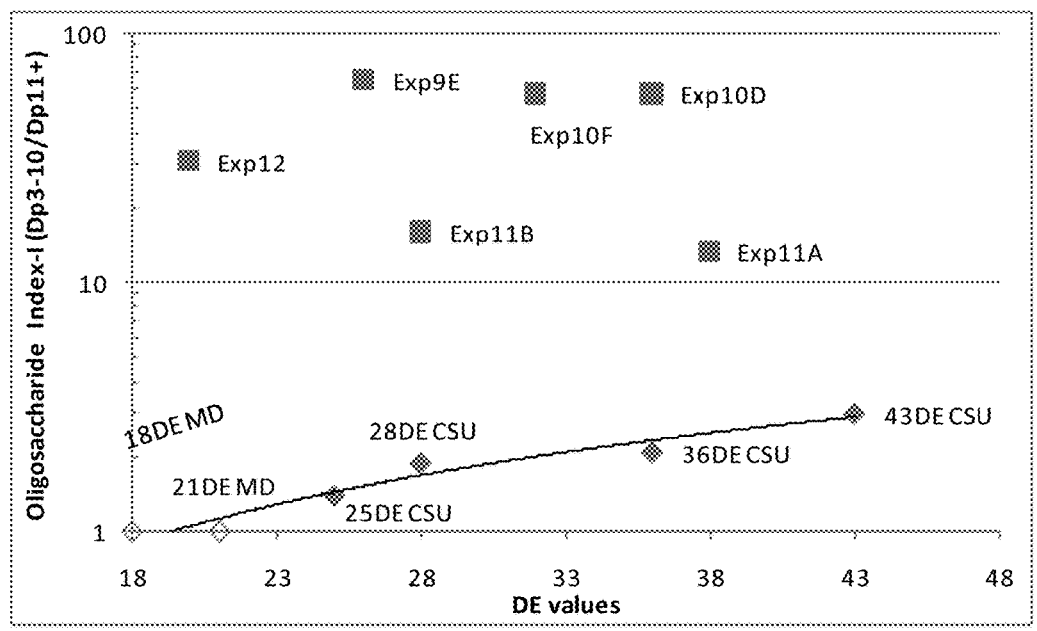
FIG. 3 is a graph of the data of certain syrup samples of the present invention and conventional starch-derived products in Examples 9, 10, 11, and 12.

FIG. 3, using the same legend as in FIG. 2, illustrates the low-viscosity reduced-sugar syrups of the present invention having a DE of about 20 DE to about 52 DE exhibit a very different carbohydrate composition, particularly significantly higher Second Oligosaccharide Index as compared to conventional syrup (CSU) and maltodextrin (MD) products at any given level of DE.

Figure 4:
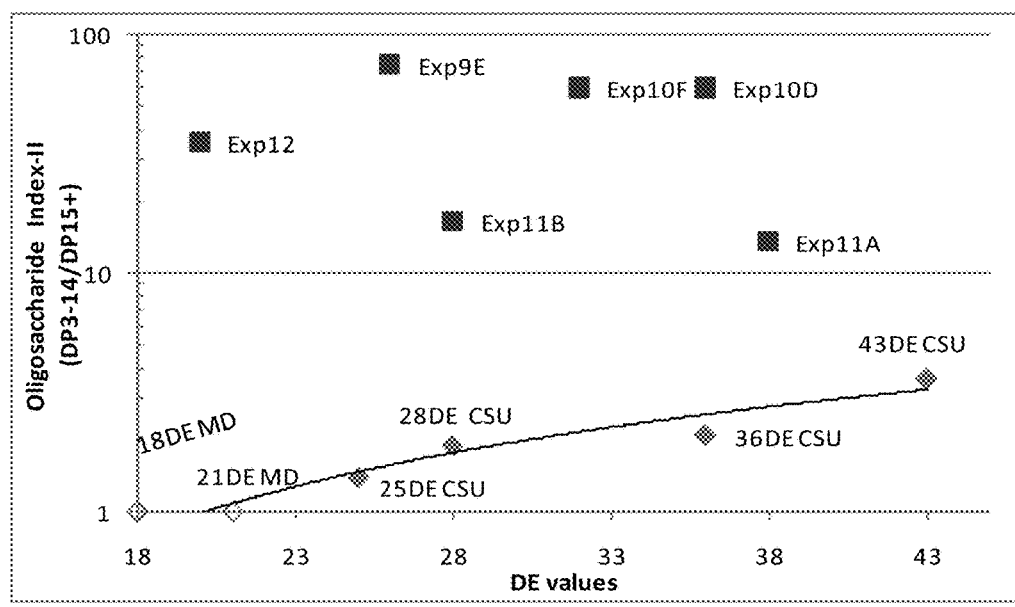
FIG. 4 is a graph of the data of certain syrup samples of the present invention and conventional starch-derived products in Examples 9, 10, 11, 12.

FIG. 4, using the same legend as in FIG. 2, illustrates the low-viscosity reduced-sugar syrups of the present invention having a DE of about 20 DE to about 52 DE exhibit a very different carbohydrate composition, particularly significantly higher First Oligosaccharide Index as compared to CSU and MD products at any given level of DE.

Examples of Applications of the Syrup

The following examples illustrate the binding, bodying, bulking, coating and water retention properties of the low-viscosity reduced-sugar syrup of the present invention. Binding properties are exemplified in examples 27, 29, 32, 34 and 39; bodying properties are exemplified in 28, 30, 31, 34 and 35; bulking properties are exemplified in examples 20-22, 24-32, and 35-38; coating properties are exemplified in example 23; and water retention properties are exemplified in examples 34, 36, 38 and 39. The property of enhancing flavors or not masking flavors is exemplified in examples 27 and 30-32. Further, with the exception of examples 22 and 39, all the examples illustrate that a food manufacturer will have challenges in making a food product if using conventional syrup having similar total mono- and di-saccharides compared to using a low-viscosity reduced-sugar syrup because of the high viscosity and high adhesiveness of the conventional syrup. The high viscosity often translates to slower pumping, flow, and other movement in food processing, and the high adhesiveness often translates to sticking to equipment, thereby reducing line speeds and increasing operational costs. These food manufacturing problems are absent when a low-viscosity reduced-sugar syrup having similar total mono- and di-saccharides as the conventional syrup is used instead.

The low-viscosity reduced-sugar syrups of the present invention, while reducing the use of sugar in foods and beverages, still provides certain functionalities that sugar possesses. As an example, besides sweetening, sugar has many functional roles in food, such as, for example, bread would lose its freshness and dry out without sugar; the shelf life of bread is extended because sugar causes water to be retained longer in the bread (i.e., sugar binds water). In products such as biscuits and hard caramel, which contain small amounts of moisture and large amounts of sugar, the relative moisture level is lower than the ambient humidity. Without protective packaging, these products will absorb moisture from the air (www.nordicsugar.com/industry/on-a-technical-level/moisture-retention). The carbohydrate compositions of the present invention and syrups having the carbohydrate compositions thereof not only allow for a reduction in sugar in foods and beverages, but retain moisture, which is useful in foods, such as breads, bars, and other bakery and confectionary products. Contrary to conventional syrups where an increase in DE results in increased moisture retention (i.e., humectancy) and generally accompanied with increased moisture pickup (i.e., hygroscopicity), the carbohydrate compositions of the present invention and syrups thereof did not increase hygroscopicity, but increased moisture retention, as shown in FIG. 5.

Example 20—Use of Low-Viscosity Reduced-Sugar Syrup in Yogurt

About one half gallon of fat free milk, about 2 cups of non-fat instant dry milk powder, about 1 cup of commercial 55 high fructose corn syrup (HFCS) and about 8 oz. of commercial plain yogurt were used to make the control yogurt. The recipe of the reduced sugar yogurt was about one half gallon of fat free milk, about 2 cups of non-fat instant dry milk powder, about 1 cup of low-viscosity reduced-sugar syrup of Example-9D, about 200 ppm of rebiana (zero-calorie, natural sweetener), and about 8 oz. of commercial plain yogurt. The fresh milk, dry milk powder and syrup (control or the syrup of the present invention and rebiana) were mixed and heated to about 185° F. to about 195° F. for about 10 minutes, cooled to about 118° F. to about 122° F., then gently folded in the plain yogurt. The mixture was allowed to ferment at about 118° F. to about 122° F. for about 6 hours before cold storage at about 40° F. overnight. The resulting reduced sugar yogurt had a very creamy and smoother texture than the control yogurt, the tartness came through nicely, and it had an excellent spoonability. The yogurt made with the syrup of the present invention contained about 10 grams of sugar per about 4 oz. serving compared to about 17 grams of sugar of the control recipe.

Example 21—Use of Low-Viscosity Reduced-Sugar Syrup as a Bulking Agent for Erythritol Erythritol is a family of polyols which has zero caloric value but limited human digestive tolerance, which greatly restricts its applications in food products. Erythritol also has limited solubility by itself (less than about 35% DS at about room temperature) or in conventional corn syrup. However, a high solids concentration of up to about 84% DS, clear and stable solution was achieved by blending erythritol with syrups of this invention. The low-viscosity reduced-sugar syrup of Example-10D was blended with erythritol at ratios of about 90 parts syrup/about 10 parts erythritol, about 80 parts syrup/about 20 parts erythritol and about 75 parts syrup/about 25 parts erythritol (on dry weight basis) and co-evaporated at about 95° C. to about 84% DS. The resulting syrup had very low viscosity, for example, at about 84% DS, the blended syrup had about 2950 cPs at about 140° F. This example demonstrated the use of the low-viscosity reduced-sugar syrup as an effective bulking agent for polyols, such as erythritol, to produce a reduced calorie, low sweet, low viscosity and all natural syrup.

Example 22—Use of Low-Viscosity Reduced-Sugar Syrup as a Compatible Syrup with Other Nutritive Sweeteners The syrup of this invention of Example-9B was blended with a 55 HFCS at different dry solid concentration (up to about 84% DS) and different ratios (about 75/25 and about 50/50) and resulted in very stable and flowable syrup at about room temperature. The syrup of this invention of Example-9B was also blended with liquid sucrose at different ratios (about 10/90, about 20/80, about 35/65, about 50/50 and about 75/25) and co-evaporated to about 85% DS. The resulting blended syrup was flowable and stable at much higher solids concentration than liquid sucrose by itself. This example demonstrated that the low-viscosity reduced-sugar syrup of this invention can be used as an compatible syrup to sweeteners such HFCS or sucrose to retard crystal formation and increase stability at much higher solids content providing food manufacturers with the flexibility of applications.

Example 23—Use of Low-Viscosity Reduced-Sugar Syrup in Sweetened Ready-to-Eat Cereal The sweetener recipe of the control ready-to-eat cereal was about 5.4% honey, about 75.6% sugar and about 19.0% water, heated to boiling, poured over about 188.7 grams base cereal in a drum coater to coat for about 90 seconds at about 10 rpm, and then transferred to mesh screen to dry in a forced air oven at about 250° F. for about 35 minutes. Another control recipe formulated with commercially available corn syrup had about 3.9% honey, about 48.8% sugar, about 34.2% 36 DE corn syrup and about 13.1% water, heated to boiling, poured over about 115.8 grams of base cereal to coat and dry as described for the sugar-only control cereal. After drying, the coated ready-to-eat cereals were examined for stuck clusters, yield and bulk density. The sweetener recipe of the low-viscosity reduced-sugar syrup of Example-9D coated cereal was about 3.9% honey, about 50.2% sugar, about 33.2% low-viscosity reduced-sugar syrup and about 12.7% water, heated to boiling, poured over about 115.8 grams of base cereal to coat and dry as described for both control cereals. The resulting cereals all contained about 9 grams of sugar per about 28 grams serving and had a very similar taste. The low-viscosity reduced-sugar sweetened cereals had a much better bulk density (about 142 grams per about 24 oz. container) than the sugar-only control cereal (about 124 grams per about 24 oz. container), and the 36 DE corn syrup sweetened control cereals contained about 135 grams. It was also observed that the low-viscosity sugar-reduced syrup was less sticky to the coating drum and much easier to handle as compared to the 36 DE corn syrup sweetened control cereals.

Example 24—Use of Low-Viscosity Reduced-Sugar Syrup in Muffins

The recipe of the control muffins was about 32.1% all-purpose flour, about 25% heavy whipping cream, about 14.1% fat free milk, about 22.7% honey, about 5% eggs, about 0.3% vanilla extract, about 0.6% baking soda and about 0.2% salt. The recipe of the sugar reduced muffins was about 32.1% all-purpose flour, about 25% heavy whipping cream, about 12.6% fat free milk, about 24.1% low-viscosity reduced-sugar syrup of Example-9E, about 5% eggs, about 0.3% vanilla extract, about 0.6% baking soda and about 0.2% salt. The resulting muffins had very similar texture, mouth-feel and flavor, both had about 139 Kcal per about 48 grams muffin, and both had about 13.9% calories from fat. The control muffins had about 9.4 grams of sugar, while the sugar reduced muffins had about 1.5 grams of sugar per muffin, which was about an 84% reduction of the added sugar.

Example 25—Use of Low-Viscosity Reduced-Sugar Syrup in Hard Boiled Candy

The recipe of the control candy was about 49.0% sugar, about 29.1% 43 DE corn syrup, about 21.8% water, about 0.04% flavor, about 0.01% color and about 0.03% citric acid. The recipe of the reduced sugar candy was about 32.2% sugar, about 45.9% low-viscosity reduced-sugar syrups of Example-10A and Syrup-8A, about 21.8% water, about 0.04% flavor, about 0.01% color and about 0.03% citric acid. The resulting candies all set up within about 20 minutes, were very easy to unmold, both had excellent clarity, no cold flow attributable to the relatively low hygroscopicity of the carbohydrate compositions of the present invention, with the reduced-sugar candy having about 25% less sugar than the control candy.

Example 26—Use of Low-Viscosity Reduced-Sugar Syrup in Gelatin Candy

The recipe of the control gelatin candy was about 17.4% gelatin solution, about 50.7% 43 DE corn syrup, about 30.0% sugar, about 0.6% flavor, about 0.01% color, about 0.03% citric acid and about 1.2% water. The recipe of the reduced sugar gelatin candy was about 17.4% gelatin solution, about 50.7% low-viscosity reduced-sugar syrup of Example-9E and Syrup-8A, about 30.0% sugar, about 0.6% flavor, about 0.01% color, about 0.03% citric acid and about 1.2% water. The resulting gelatin candies deposited similarly, had comparable clarity, soft and chewy, with the reduced sugar gelatin candy having about 25% less sugar than the control.

Example 27—Use of Low-Viscosity Reduced-Sugar Syrup in Toffee

The recipe of the control toffee was about 47.1% sugar, about 48.4% butter, about 3.5% 43 DE corn syrup, about 0.6% salt, about 0.4% vanilla extract. The recipe of the reduced sugar toffee was about 34.6% sugar, about 48.4% butter, about 16% low-viscosity reduced-sugar syrup of Example-9E, about 0.6% salt, about 0.4% vanilla extract. The resulting toffees both caramelized very well, with the reduced sugar toffee having about 25% less sugar than the control, yet still provided very pleasant sweetness.

Example 28—Use of Low-Viscosity Reduced-Sugar Syrup in Sorbet

The recipe of the control sorbet was about 40.0% water, about 30.0% sugar, about 4.0% lemon juice, about 26.0% pineapple juice. The recipe of the reduced sugar sorbet was about 38.5% water, about 15.0% sugar, about 15.0% low-viscosity reduced-sugar syrup of Example-9E or Syrup-8A, about 5.0% lemon juice, about 26.5% pineapple juice. The resulting reduced sugar sorbet was very creamy, no visual ice crystal on surface and scooped easily; vs. the control sorbet was gritty, not creamy, had large ice crystals on the surface and on the tongue.

Example 29—Use of Low-Viscosity Reduced-Sugar Syrup in Crunchy Granola Bars

The recipe of the control bar was about 48.2% 43 DE corn syrup, about 1.8% water, about 34.5% rolled oats and about 15.5% crispy rice. The recipe of the reduced sugar bar was about 49.1% low-viscosity reduced-sugar syrup of Example-4, about 1.0% water, about 34.5% rolled oats and about 15.5% crispy rice. The reduced sugar granola bars had short texture, were harder and more brittle than the control bars and had about 25% less sugar than the control.

Example 30—Use of Low-Viscosity Reduced-Sugar Syrup in Savory Sauces

A savory sauce was made by blending 20 grams (g) of either the control (36DE corn syrup) or the low-viscosity reduced-sugar syrup of Example-4 and 10 g of Tamari Organic Wheat Free Soy Sauce with a whisk in a stainless steel bowl. Both sauces gave a pleasant appearance and flavor. However, the sauce made with the control syrup had a pronounced sweetness which was not desirable for this product. In comparison, the sauce made with the low-viscosity reduced-sugar syrup of the current invention had no sweetness and a more desirable overall taste.

Example 31—Use of Low-Viscosity Reduced-Sugar Syrup in Vinaigrette Dressing

A Vinaigrette dressing was made by whisking about 30 g of low-viscosity reduced-sugar syrup of Example-4 with about 30 g white vinegar, about 0.4 g red pepper flakes and about 0.5 g salt in a bowl. This dressing had notes of a rich natural taste with noticeable lack of sugar notes. The dressing had a freshness not noticeable in traditional formats when corn syrup was used.

Example 32—Use of Low-Viscosity Reduced-Sugar Syrup in Savory Bar/Clusters

A glaze sauce was made by gently cooking about 225 g low-viscosity reduced-sugar syrup of Example-4, about 110 g vegetable base, about 55 g canola oil, about 35 g ground flax seed, about 3 g salt and about 0.4 g red pepper flakes in a kettle. A savory bar was made by cooking the glaze sauce to boil while stirring in dry ingredients of about 112.5 g Inulin Breakfast Cereal Flakes, about 50 g Crunchy Wheat & Barley Cereal, about 37.5 g Prosante, about 37.5 g Fiber Krunch, about 10 g freeze dried tomato pieces, about 12.5 g freeze dried corn kernel, about 15 g shredded dry carrots. After all dry ingredients were coated, the mixture was placed in parchment lined half sheet pan, pressed with rolling pin to produce a level surface and lowed to set for about 5 min before cutting to desired size of about ½"×3½" and individually wrapped. To make clusters, the glaze sauce and dry ingredient mixture was poured on to parchment lined half sheet pan, using spoons pull to form about quarter size rustic clusters, sprinkle with kosher salt, baked in about 300° F. oven for about 4 minutes, rotate-baked for about another 4 minutes then removed from the oven and cooled at room temperature for about 30 minutes. The low-viscosity reduced-sugar syrup of this invention allowed the ability to build the binding glaze without adding any sweet-masking agents that were otherwise needed when using traditional sweet corn syrup. The savory bar and clusters gave pleasant flavor and taste.

Example 33—Use of Low-Viscosity Reduced-Sugar Syrup as a Carrier for High Potency Sweetener High potency sweeteners are often added to foods and beverage in very small quantities to achieve the desired sweetness. To achieve a precise addition of small quantities, high potency sweeteners are often pre-dissolved in a carrier, for example, water. However, some high potency sweeteners, such as rebiana have a very low solubility and/or stability in water. Rebiana is typically in dry, fine powder forms making it difficult for food manufactures to handle. This example demonstrated the use of the low-viscosity reduced-sugar syrup as an effective carrier for high potency sweeteners to enhance processes. About one pound of about 30% (w/w) rebiana solution was added to about 149 lbs of low-viscosity reduced-sugar syrup of Example-4 at about 158° F. and agitated until well mixed. The resulting syrup contained about 2000 ppm of rebiana and was shelf stable for at least about 3 months at about 120° F.

Example 34—Use of Low-Viscosity Reduced-Sugar Syrup in Meal Replacement Bars The recipe of control bar has about 18.7% soy protein isolate, about 33.6% high fructose syrup (55 HFCS, about 99% sugar, about 77% dry solid), about 26.7% high maltose corn syrup (63DE, about 69% sugar, about 80% dry solid), about 5.4% maltodextrin, about 1.4% novagel, about 5% vitamin/mineral mix, about 0.6% salt, about 7.9% honey and about 0.7% key lime flavor. The recipe of sugar reduced bar has about 18.7% soy protein isolate, about 64.3% low-viscosity reduced-sugar syrup Example-4 and Syrup-8A, about 1.2% water, about 1.4% novagel, about 5% vitamin/mineral mix, about 0.6% salt, about 7.9% honey, about 0.7% key lime flavor and about 0.19% rebiana. Sugar concentration of the bar with rebiana and the low-viscosity reduced-sugar syrup contains about 15.7-18.7% sugar, resulting in about a 60-66% sugar reduction from the about 46.8% sugar in the control bar. The sugar-reduced bar has a similar taste to that of control.

Example 35—Use of Low-Viscosity Reduced-Sugar Syrup in Meal Replacement Dairy Beverage The recipe of the control beverage was about 75.0% skim milk, about 10.5% nonfat dry milk, about 0.5% lecithin, about 1% maltodextrin, about 0.54% cocoa powder, about 0.2% trisodium citrate, about 0.06% salt, about 8% high fructose syrup (55 HFCS, about 98% sugar, about 77.1% dry solid), about 4% high maltose corn syrup (about 69% sugar, about 80% dry solid), about 0.1% cinnamon, and about 0.1% vanilla. The recipe of the sugar reduced beverage was about 75.0% skim milk, about 10.5% nonfat dry milk, about 12% low-viscosity reduced-sugar syrup of Example-9D, about 0.54% lecithin, about 1% maltodextrin, about 0.54% cocoa powder, about 0.2% trisodium citrate, about 0.06% salt, about 0.1% cinnamon, about 0.1% vanilla, and about 0.02% rebiana. The sugar reduced beverage with rebiana and the low-sugar-low-viscosity syrup of the current invention had a very smooth, satisfying mouthfeel, blended flavors well and contained about 11% of added sugar, resulting in about a 76% sugar reduction from about 46% added sugar in the control meal replacement beverage.

Example 36—Use of Low-Viscosity Reduced-Sugar Syrup in Raspberry Jam

The recipe of control jam has about 39.1% fruit, about 32.1% corn syrup (43DE, about 35% sugar, about 80% dry solid), about 13% sugar, about 0.5% pectin, about 2.6% water, about 11.7% HFCS (42 HFCS, about 99% sugar, about 71% dry solid), about 0.2% potassium sorbate, about 0.2% sodium benzoate, about 0.6% citric acid solution (50% w/w). The reduced sugar jam has about 28.1% fruit, about 57.9% low-sugar-low-viscosity syrup Example-4 or Syrup-8A, about 0.5% pectin, about 2.5% water, about 0.2% sodium sorbate, about 0.2% sodium benzoate, about 0.6% citric acid solution and about 0.13% rebiana. Sugar concentration of the sugar reduced jam with rebiana and the low viscosity reduced sugar corn syrup has about 12.6-15.9% sugar, resulting in about a 41-54% sugar reduction from the about 27.1% sugar in the control jam.

Example 37—Use of Low Viscosity Reduced-Sugar Syrup in Ice Cream

The recipe of control ice cream has about 12% fat, about 10% milk solid, about 13% sucrose, about 5% corn syrup (36DE, about 27% sugar, about 80% dry solid) and about 0.35% stabilizer. The recipe of the sugar reduced ice cream has about 12% fat, about 10% milk solid, about 5% sucrose, about 13% low-sugar-low-viscosity syrup Example-4 or Syrup-8A, about 0.35% stabilizer and about 0.06% rebiana. Sugar concentration of the sugar reduced ice cream with rebiana and the low-sugar-low-viscosity syrup contains about 6.9-7.5% sugar, about a 47-51% sugar reduction from the about 14.1% sugar in the control ice cream.

Example 38—Use of Low-Viscosity Reduced-Sugar Syrup in Chocolate Chip Cookies

The recipe of the control chocolate chip cookies has about 31.6% flour, about 23.7% sugar, about 18.9% shortening, about 2.2% egg solids, about 5.4% water, about 0.4% salt, about 0.2% sodium bicarbonate, about 0.3% flavor, and about 17.4% chocolate chips. The reduced sugar chocolate chip cookies has about 31.4% flour, about 29.4% low-viscosity reduced-sugar syrup Example-4 or Syrup-8A, about 18.8% shortening, about 2.2% egg solids, about 0.4% salt, about 0.2% sodium bicarbonate, about 0.3% flavor, about 17.3% chocolate chips and about 0.1% rebiana. Sugar concentration of the sugar-reduced chocolate chip cookies with rebiana and the low-viscosity reduced-sugar syrup contains about 4.2-5.6% sugar, about 76-82% sugar reduction from the control chocolate chip cookies.

Example 39—Enhanced Smoked Turkey Product

Water holding capacity in enhanced meats yields juicier products, which consumers might perceive as desirable. Often salts and sugars are used in brines to prepare enhanced meats. The low-viscosity reduced-sugar syrup was incorporated into an enhanced smoked turkey recipe, replacing some of the salts and sugars normally used. The control brine contained about 79.9% water, about 10.5% sugar, and about 9.6% salt by weight. The syrup-based brine comprised about 76.8% water, about 13.6% low-viscosity reduced-sugar syrup of Example-9D (about 10.5% on a dry basis), and about 9.6% salt. The brines were injected into the turkeys such that the brine comprised about 16.67% of the final weight. The turkeys were tumbled in a vacuum for one hour, vacuum packaged, and cooked by steam. The final weight yields were comparable for the control and sample turkeys at about 85.7% and about 83.8% of their original weights, respectively.

Example 40—Use of Low-Viscosity Reduced-Sugar Syrup in Chewy Sweet Granola Bars

A chewy sweet granola bar using Syrup '410 (not de-ashed) to replace conventional syrup and granular sugar was compared to a control bar using conventional 43% HMCS (commercially available from Cargill, Incorporated, Wayzata, Minn.) and granular sugar. The formulas (Table 18) showed about 33% sugar reduction (8 g vs 12 g per 35 g serving size) in the bar products using Syrup '410 compared to the control.

TABLE 18

| Formulas of chewy sweet bars | | |
|---|---|---|
| Treatment | Control | Syrup '410 |
| Binding syrup, g | | |
| 43% HMCS | 28 | 0 |
| Syrup '410 | 0 | 31 |
| Honey | 6 | 6 |
| Granulated sugar | 3 | 0 |
| Canola oil | 2.2 | 2.2 |
| Lecithin | 0.65 | 0.65 |
| Salt | 0.6 | 0.6 |
| Vanilla | 0.45 | 0.45 |
| Total | 40.9 | 40.9 |
| Granola base (dry), g | | |
| Granola blend | 29 | 29 |
| Rice Crisp | 9.1 | 9.1 |
| Raisins | 6.5 | 6.5 |
| Whole almond | 6.1 | 6.1 |
| Dry roast peanut | 4 | 4 |
| Sunflower seeds | 2.4 | 2.4 |
| Cranberries | 2 | 2 |
| Total | 59.1 | 59.1 |
| Finished bars | | |
| Moisture, % | 7.4 | 8.0 |
| Nutrition (g/35 g serving) | | |
| Sugar | 12 | 8 |

The bars were prepared in the following steps: 1. Combine the base ingredients in a mixing bowl; 2. Combine the oil and lecithin in a separate container; 3. Weigh the binder ingredients minus the flavors in a pot; 4. Heat the binder ingredients minus the flavors, oil and lecithin on the stove top up to 160° F. while mixing; 5. Record the temperature of the binder; 6. Take a brix reading of the binder and record; 7. Remove the binder from the heat and add the flavors and oil/lecithin mixture while mixing; 8. Pour the binder over the base and mix well; 9. Press into bar p"n ("5"L×8"W×⅝"D); 10. Cool in refrigerator or freezer and cut into bars; and, 11. Wrap bars in metallic film using the Stratus bar wrapper and stored at ambient temperature.

After one week and again after one month, the hardness of each bar was quantified using a texture analyzer (TA.XT2, TA55 probe, 50% compression, 60-second hold). Three hardness readings were taken for each bar. As shown in Table 19 below, the hardness of the bars after storing for one week was 884.54 gram/inch$^2$ (control with 43% HMCS) compared to 442.58 gram/inch$^2$ (Syrup '410 (not de-ashed)), and after storing for one month the hardness of the bars was at 993.01 gram/inch$^2$ (control) compared to 485.68 gram/inch$^2$ (Syrup '410). Bars made with Syrup '410 of the present invention were softer after storage both at one-week and at one-month than the control bars made with a conventional 43% HMCS. Bars made with Syrup '410 were twice as soft as the bars made with conventional syrup.

TABLE 19

Hardness of the bars

| Treatment | Control 43% HMCS | Syrup '410 |
|---|---|---|
| | 1 week storage | |
| g/sq in | 884.54 | 442.58 |
| | 1 month storage | |
| g/sq in | 933.01 | 485.68 |

Example 41—Use of Low-Viscosity Reduced-Sugar Syrup in Gummy Candy (Jelly Confectionery)

Either a 43 DE syrup (control), commercially available from Cargill, Incorporated, Wayzata, Minn., or Syrup '401 (de-ashed) was used to formulate gummy candies according to Table 20.

TABLE 20

Gummy candy formula

| Ingredient | as-is, g | % Solids | dry base | % Db |
|---|---|---|---|---|
| 250 bloom Gelatin A | 5.17 | 100% | 5.17 | 7.49% |
| Water (for gelatin) | 10.34 | | | |
| Syrup (43DE or Syrup '410 (de-ashed)) | 38.79 | 80% | 31.03 | 44.97% |
| Granulated sugar | 31.90 | 100% | 31.90 | 46.23% |
| Water (for sugar solution) | 11.70 | | | |
| Citric Acid (50%) | 1.80 | 50% | 0.90 | 1.30% |
| Flavor | 0.30 | 100% | 0.30 | 0.43% |
| Total | 100.00 | | 69.30 | 100.43% |
| Moisture | | | 31.7% | |
| Sugar (g/40 g serving, control) | | | 22 | |
| Sugar (g/40 g serving, Syrup '410 (de-ashed) | | | 20 | |

The gummy candies were prepared according to the following steps: 1. Preheat depositing funnel and starch mold in the oven at 200° F.; 2. Dissolve/rehydrate gelatin in water by mixing and heating the gelatin in the microwave for 30 seconds; 3. Mix sugar, syrup and second portion of water and cook until it reach 90° Brix; 4. Pour the sugar solution into a pre-tare glass beaker; 5. Once the temperature of the sugar reaches 100° C., mix in gelatin (re-heat the gelatin) into the sugar solution; 6. Add acid, color (when necessary) and flavor; and 7. Pour the candy mass into the depositing funnel and deposit the candy to the starch mold.

After cooling to ambient temperature, the candies were measured for firmness and springiness using a texture analyzer (TA.XT2, TA55 probe, 50% compression, 60-second hold). The first force measurement provides "Firmness" data while the force recorded at the end of 60-second hold was compared against the first force data, providing the "Springiness" of the product. The candies were stored in sealed plastic bags at ambient pressure, and firmness and stringiness were measured after one month and at four months.

Table 21 shows the Firmness of the candies on Day 0 was 182 grams (control) compared to 152 grams (Syrup '410), and after storing for one month the Firmness of the candies was 370 grams (control) compared to 255 grams (Syrup '410) and after storing for four months the Firmness was 430 grams (control) compared to 365 (Syrup '410). The Springiness of the candies on Day 0 was 41% (control) compared to 45% (Syrup '410), and after storing for one month the Springiness of the candies was 41% (control) compared to 45% (Syrup '410) and after storing for four months the Springiness was 37% (control) compared to 47% (Syrup '410). Gummy candies made with Syrup '410 (de-ashed) remained less firm (i.e., softer) with higher springiness than the candies made with a conventional 43 DE syrup (control) over a four-month period stored in a sealed bag under ambient conditions. The sensory test showed similar sweetness, even though the candies made with Syrup '410 (de-ashed) contained 10% less sugar per serving.

TABLE 21

Texture measurements of gummy candies

| Measurements | Time Month | Sample Control | Syrup '410 |
|---|---|---|---|
| Firmness (g) | 0 | 182 | 152 |
| | 1 | 370 | 255 |
| | 4 | 430 | 365 |
| Springiness (%) | 0 | 41 | 45 |
| | 1 | 37 | 47 |
| | 4 | 39 | 46 |

Figure 6:
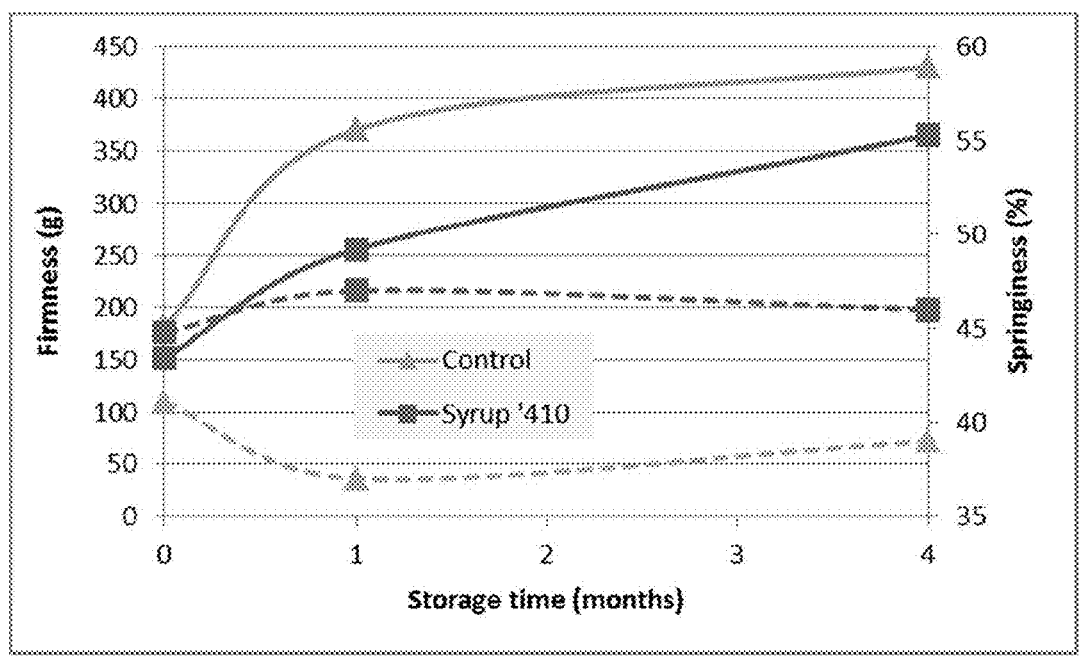
FIG. 6 is a graph of gummy candies made with a conventional 43DE syrup and a syrup sample of the present invention.

FIG. 6 is a graph representative of Table 21. The solid line represents "Firmness" and the dotted line represents "Springiness" of the gummy candies stored for up to four months in sealed bags at ambient conditions.

In general, based on the various examples set forth above, the carbohydrate compositions of the present invention increase softness, or conversely decrease hardness, by at least 10% of foods containing about 10% to 70% moisture (w/w) and less than 50% total mono- and di-saccharides (w/w) when more than 5% (w/w) of the carbohydrate compositions are incorporated into such foods.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A carbohydrate composition comprising:
   a. no more than 25% total mono- and di-saccharides, on a dry weight basis;
   b. total oligosaccharides with a degree of polymerization from 3 to 4, on a dry weight basis, ranges from about 50% to about 75%;
   c. less than 10% of polymeric carbohydrates with degree of polymerization of at least 11; and
   d. a ratio of DP2/DP5 of at least 4.2,
   wherein the carbohydrate composition has a higher moisture retention during desorption at relative humidity of less than 90% at 25° C. and at ambient pressure, compared to a 36 DE or a 43 DE conventional syrup.

2. The carbohydrate composition of claim 1, having a ratio of DP3/DP5 of greater than 4.5.

3. A syrup or dry product comprising the carbohydrate composition of claim 1.

4. The syrup of claim 3, having a viscosity of less than about 10,000 cPs, or having a viscosity of less than about 8,000 cPs, when measured at a temperature of about 100° F. and about 78% DS.

5. A carbohydrate composition comprising:
   a. no more than 25% total mono- and di-saccharides, on a dry weight basis;
   b. total oligosaccharides with a degree of polymerization from 3 to 4, on a dry weight basis, ranges from about 50% to about 75%;
   c. less than 10% of polymeric carbohydrates with degree of polymerization of at least 11; and
   d. a ratio of DP2/DP5 of at least 4.2,
   wherein the carbohydrate composition has a similar moisture retention during adsorption at relative humidity of more than 5% to 90% at 25° C. and at ambient pressure, compared to a conventional 36 DE syrup.

6. The carbohydrate composition of claim 5, having a ratio of DP3/DP5 of greater than 4.5.

7. The syrup or dry product comprising the carbohydrate composition of claim 5.

8. The syrup of claim 7, having a viscosity of less than about 10,000 cPs, or having a viscosity of less than about 8,000 cPs, when measured at a temperature of about 100° F. and about 78% DS.

9. A carbohydrate composition comprising:
   a. no more than 25% total mono- and di-saccharides, on a dry weight basis;
   b. total oligosaccharides with a degree of polymerization from 3 to 4, on a dry weight basis, ranges from about 50% to about 75%;
   c. less than 10% of polymeric carbohydrates with degree of polymerization of at least 11; and
   d. a ratio of DP2/DP5 of at least 4.2,
   wherein the carbohydrate composition increases softness, or conversely decreases hardness, by at least 10% of foods containing about 10% to about 70% moisture (w/w) and less than about 50% total mono- and di-saccharides (w/w) when more than about 5% (w/w) of the carbohydrate compositions are incorporated into such foods.

10. The carbohydrate composition of claim 9, having a ratio of DP3/DP5 of greater than 4.5.

11. The syrup or dry product comprising the carbohydrate composition of claim 9.

12. The syrup of claim 11, having a viscosity of less than about 10,000 cPs, or having a viscosity of less than about 8,000 cPs, when measured at a temperature of about 100° F. and about 78% DS.

13. A food product, beverage product, feed product, or pharmaceutical or over-the-counter product comprising the carbohydrate composition of claim 1.

14. A food product, beverage product, feed product, or pharmaceutical or over-the-counter product comprising the syrup of claim 5.

15. A food product, beverage product, feed product, or pharmaceutical or over-the-counter product comprising the carbohydrate composition of claim 9.

* * * * *